United States Patent
Sinha

(10) Patent No.: US 10,004,561 B2
(45) Date of Patent: Jun. 26, 2018

(54) METHOD FOR GENETIC DETECTION USING INTERSPERSED GENETIC ELEMENTS: A MULTIPLEXED DNA ANALYSIS SYSTEM

(71) Applicant: LIFE GENETICS LAB, LLC, New Orleans, LA (US)

(72) Inventor: Sudhir Sinha, Matairie, LA (US)

(73) Assignee: LIFE GENETICS LAB, LLC, New Orleans, LA (US)

( * ) Notice: Subject to any disclaimer, the term of this patent is extended or adjusted under 35 U.S.C. 154(b) by 0 days. days.

(21) Appl. No.: 14/054,680

(22) Filed: Oct. 15, 2013

(65) Prior Publication Data

US 2014/0127696 A1 May 8, 2014

Related U.S. Application Data

(60) Provisional application No. 61/714,088, filed on Oct. 15, 2012.

(51) Int. Cl.
| | |
|---|---|
| *C12Q 1/68* | (2018.01) |
| *A61B 18/24* | (2006.01) |
| *A61B 18/00* | (2006.01) |
| *A61B 18/22* | (2006.01) |

(52) U.S. Cl.
CPC .. *A61B 18/245* (2013.01); *A61B 2018/00345* (2013.01); *A61B 2018/00577* (2013.01); *A61B 2018/2211* (2013.01); *A61B 2018/2238* (2013.01)

(58) Field of Classification Search
None
See application file for complete search history.

(56) References Cited

U.S. PATENT DOCUMENTS

| | | |
|---|---|---|
| 6,316,610 B2 | 11/2001 | Lee et al. |
| 7,183,056 B2 | 2/2007 | Park et al. |
| 7,794,983 B2 | 9/2010 | Sinha et al. |
| 8,614,061 B2 | 12/2013 | Brabetz et al. |
| 8,728,736 B2 | 5/2014 | Leamon et al. |
| 8,771,952 B2 | 7/2014 | Bohme et al. |
| 2008/0206755 A1* | 8/2008 | Sinha et al. ............ 435/6 |
| 2008/0286773 A1* | 11/2008 | Bender .......... C12Q 1/6858 435/6.12 |
| 2011/0143347 A1 | 6/2011 | Bohme et al. |
| 2011/0306505 A1 | 12/2011 | Chang et al. |
| 2012/0122093 A1 | 5/2012 | Hennessy et al. |
| 2013/0123120 A1 | 5/2013 | Zimmermann et al. |
| 2014/0243225 A1 | 8/2014 | Shewale et al. |

OTHER PUBLICATIONS

LaRue et al. (INNULs: A Novel Design Amplification Strategy for Retrotransposable Elements for Studying Population Variation, Hum Hered. 2012;74(1):27-35. doi: 10.1159/000343050. Epub Oct. 20, 2012).*

Vallone et al. (A multiplex allele-specific primer extension assay for forensically informative SNPs distributed throughout the mitochondrial genome, Int J Legal Med. Jun. 2004;118(3):147-57. Epub Feb. 4, 2004).*

Butler et al. (Constructing STR Multiplex Assays, Forensic DNA Typing Protocols, vol. 297 of the series Methods in Molecular Biology, pp. 53-65, Dec. 31, 2005).*

Butler et al. (The Development of Reduced Size STR Amplicons as Tools for Analysis of Degraded DNA, J Forensic Sci. Sep. 2003;48(5):1054-64).*

Weigand et al. (Less is more—length reduction of STR amplicons using redesigned primers, Int J Legal Med. 2001;114(4-5):285-7).*

Grubweiser et al. (A new "miniSTR-multiplex" displaying reduced amplicon lengths for the analysis of degraded DNA, Int J Legal Med. Mar. 2006;120(2):115-20. Epub Jul. 13, 2005).*

Hill et al. (Characterization of 26 miniSTR loci for improved analysis of degraded DNA samples, J Forensic Sci. Jan. 2008;53(1):73-80. Epub Nov. 13, 2007).*

Fondevilla et al. (Challenging DNA: Assessment of a range of genotyping approaches for highly degraded forensic samples, Forensic Science International: Genetics Supplement Series, vol. 1, Issue 1, Aug. 2008, pp. 26-28).*

Coble et al. (Characterization of New MiniSTR Loci to Aid Analysis of Degraded DNA, J Forensic Sci, Jan. 2005, vol. 50, No. 1).*

Tsukada et al. (Multiplex short tandem repeat typing in degraded samples using newly designed primers for the TH01, TPOX, CSF1PO, and vWA loci, Leg Med (Tokyo). Dec. 2002;4(4):239-45).*

Gill et al. (The evolution of DNA databases—recommendations for new European STR loci, Forensic Sci Int. Jan. 27, 2006;156(2-3):242-4. Epub Jul. 5, 2005).*

Hughes-Stamm et al. (Assessment of DNA degradation and the genotyping success of highly degraded samples, Int J Legal Med. May 2011;125(3):341-8. doi: 10.1007/s00414-010-0455-3. Epub Apr. 24, 2010).*

(Continued)

*Primary Examiner* — Aaron A Priest
(74) *Attorney, Agent, or Firm* — Robert E. Bushnell, Esq.

(57) ABSTRACT

By utilizing a Mini-Primer strategy targeting the target site duplication (TSD) sequence of retrotransposons, INNUL markers, which include SINEs, LINEs, and SVAs, can be effectively used as markers for human identification and bio-ancestry studies regardless of the size of the inserted element. The size of the amplicons for INNULs and the difference between allelic states can be reduced substantially such that these markers have utility for analyzing high and low quality human DNA samples. A 15 RE marker and Amelogenin (for sex determination) multiplex for a single tube amplification of DNA, in four color detection was successfully designed. The multiplex provided power of discrimination suitable for forensic and paternity analysis. In addition, sensitivity of detection can enable human identity and bio-ancestry studies on forensic and anthropological samples. Depending on the distribution of the alleles in global populations, INNULs can be selected for human identity testing or for bio-ancestry studies.

31 Claims, 13 Drawing Sheets

(56) References Cited

OTHER PUBLICATIONS

Novick et al. (Polymorphic human specific Alu insertions as markers for human identification, Electrophoresis. Sep. 1995;16(9):1596-601).*

Mamedov et al. (A new set of markers for human identification based on 32 polymorphic Alu insertions, Eur J Hum Genet. Jul. 2010;18(7):808-14. Epub Feb. 24, 2010).*

Ustyugova et al. (Cell line fingerprinting using retroelement insertion polymorphism, Biotechniques. Apr. 2005;38(4):561-5).*

LaRue et al. (A Validation Study of the Qiagen Investigator DIPplex® Kit; An INDEL-based Assay for Human Identification, Int J Legal Med 126 (4), 533-540. Jan. 15, 2012).*

Pereira et al. (Insertion/deletion polymorphisms: A multiplex assay and forensic applications, Forensic Science International: Genetics Supplement Series, vol. 2, Issue 1, Dec. 2009, pp. 513-515).*

J.M. Butler, et al., The development of reduced size STR amplicons as tools for analysis of degraded DNA, J. Forensic Sci. 48(5): 1054-1064 (2003).

Collins, P.J., et al., evelopmental validation of a single-tube amplification of the 13 CODIS STR Loci, D2S1338, D19S433, and amelogenin: The AmpFSTR® Identifiler® PCR Amplification Kit, Journal of Forensic Sciences, 49(6): 1265-1277 (2004).

LaFountain, M.J., et al., TWGDAM Validation of the AmpFeSTR Profiler Plus and AmpFeSTR COfiler STR Multiplex Systems Using Capillary Electrophoresis, Journal of Forensic Sciences, 46(5): 1191-1198 (2001).

Morelli, T., et al., Validation of short tandem repeats (STRs) for forensic usage: performance testing of fluorescent multiplex STR systems and analysis of authentic and simulated forensic samples, Journal of Forensic Sciences, 46(3): 647 (2001).

Shuber, et al., A simplified procedure for developing multiplex PCRs, Genome Research 5(5): 488-493 (1995).

O. Henegariu, et al, Multiplex PCR: Critical Parameters and Step-by-Step Protocol, BioTechniques 23(3): 504-511 (1997).

Fondevila M, et al., Challenging DNA: assessment of a range of genotyping approaches for highly degraded forensic samples, Forensic Science International: Genetics Supplement Series (2008), 1(1): 26-28.

Brinkmann, B., et al., Mutation rate in human microsatellites: influence of the structure and length of the tandem repeat, The American Journal of Human Genetics, 62(6): 1408-1415 (1998).

Micka, K.A., et al., Validation of multiplex polymorphic STR amplification sets developed for personal identification applications, Journal of Forensic Sciences, 41: 582-590 (1996).

A.F.A. Smit, The origin of interspersed repeats in the human genome, Current Opinion in Genetics Development, 6(6): 743-748 (1996).

Heitzer E, et al., Establishment of tumor-specific copy number alterations from plasma DNA of patients with cancer, Int J Cancer (2013), 133: 346-56.

Batzer, M.A., et al., African origin of human-specific polymorphic Alu insertions, Proceedings of the National Academy of Sciences, 91(25): 12288 (1994).

Feng, Q., et al., Human L1 retrotransposon encodes a conserved endonuclease required for retrotransposition, Cell, 87(5): 905-916 (1996).

Gill P, et al., An assessment of whether SNPs will replace STRs in national DNA databases—joint considerations of the DNA working group of the European Network of Forensic Science Institutes (ENFSI) and the Scientific Working Group on DNA Analysis Methods (SWGDAM), Sci Justice (2004), 44(1): 51-3.

Kazazian, H.H., et al., The impact of L1 retrotransposons on the human genome, Nature Genetics, 19(1): 19-24 (1998).

LaRue BL, et al., INNULs: A Novel Design Amplification Strategy for Retrotransposable Elements for Studying Population Variation, Hum Hered (2012), 74: 27-35.

Wang, H., et al., SVA Elements: A Hominid-specific Retroposon Family, J. Mol. Biol. 354: 994-1007 (2005).

Vallone, et al., A multiplex allele-specific primer extension assay for forensically informative SNPs distributed throughout the mitochondrial genome, Int. J. Legal Med. Jun. 2004; 118(3): 147-57, Epub Feb. 4, 2004.

Syvanen, A.C., et al., Identification of individuals by analysis of biallelic DNA markers, using PCR and solid-phase minisequencing, American Journal of Human Genetics, 52(1): 46-59 (1993).

LaRue, B.L., et al., A validation study of the Qiagen Investigator DIPplex® kit; an INDEL-based assay for human Identification, International Journal of Legal Medicine, 2012, 1-8).

Shriver, M.D., et al., Ethnic-affiliation estimation by use of population-specific DNA markers, American Journal of Human Genetics, 60(4): 957 (1997).

Ustyugova, S.V., et al. (Cell line fingerprinting using retroelement insertion polymorphism. BioTechniques, 38(4): 561-565 (2005).

Novick, et al. (Polymorphic human specific Alu insertions as markers for human identification. Electrophoresis, 16(1): 1596-1601 (1995).

Mamedov, et al. (A new set of markers for human identification based on 32 polymorphic Alu insertions, European Journal of Human Genetics, 18(7): 808-814 (2010).

Burger, J., et al., DNA preservation: A microsatellite DNA study on ancient skeletal remains, Electrophoresis, 20(8): 1722-1728 (1999).

Mulero JJ, et al., Development and validation of the AmpFlSTR MiniFiler PCR Amplification Kit: a MiniSTR multiplex for the analysis of degraded and/or PCR inhibited DNA, J. Forensic Sci. (2008), 53(4): 838-852.

Golenberg, E.M., et al., Effect of Highly Fragmented DNA on PCR, Nucleic Acids Research, 24(24): 5026-5033 (1996).

Lander ES, et al., Initial sequencing and analysis of the human genome, Nature, (2001) 409(6822): 860-921.

Coble M, et al., Characterization of new miniSTR loci to aid analysis of degraded DNA, J. Forensic Sci. (2005), 50(1): 43-53.

Holland M.M., et al., Mitochondrial DNA sequence analysis—Validation and use for forensic casework, Forensic Sci Rev (1999), 11:21.

Wang, J., et al., dbRIP: A highly integrated database of retrotransposon insertion polymorphisms in humans, Human Mutation, 27(4): 323-329 (2006).

Benson, D.A., et al., GenBank, Nucleic Acids Research, 33 (suppl. 1): D34-D38 (2005).

Excoffier, L., et al., Arlequin (version 3.0): an integrated software package for population genetics data analysis, Evolutionary Bioinformatics Online, 1: 47 (2005).

Wiegand, et al., Less is more—length reduction of STR amplicons using redesigned primers, Int J Legal Med (2001) 114: 285-287.

Cheung, K.H., et al., ALFRED: an allele frequency database for diverse populations and DNA polymorphisms, Nucleic Acids Research, 28(1): 361 (2000).

Magnuson V.L., et. al., Substrate Nucleotide-Determined Non-Templated Addition of Adenine by Taq DNA Polymerase: Implications for PCR-Based Genotyping and Cloning, BioTechniques 21(4): 700-709 (1996).

Oostdik K, et al., Developmental validation of the PowerPlex® Fusion System for analysis of casework and reference samples: A 24-locus multiplex for new database standards, Forensic Science International: Genetics (2014), 12: 69-76.

Hill C., et al., Characterization of 26 MiniSTR Loci for Improved Analysis of Degraded DNA Samples, Journal of Forensic Science 53(1): 73-80 (2008).

McGinnis, S., et al., BLAST: at the core of a powerful and diverse set of sequence analysis tools, Nucleic Acids Research, 32(suppl 2): W20-W25 (2004).

* cited by examiner

FIG. 3

A. Filled Site Reaction of marker Ya5ac2305:

CAAACTATCGGTATAATCTCTAATTGTCTCATTATAAAGTATTCTATTTCTATAGGACAGGTAATAATC
CAGAAAAATGAAACTAAGATGATCAAAACCTGTAGTTAATACTTTAAAATACAATCCAACACCATTTAAT
CTTCTGAGTTGGTGACACTCCAATTTCTCTCTAAGGTTCCTTAAGAGTTGTAATGGGGGGCGG
GTCTACGGGTTAATCCAGCATTGGAG
GCCAGCGCGGGTATAGCAGAGCATGAGCATCCGGTAAACCGTCTCT
ACTAATACAAAATAGCGGGGCTAGTGCGGGGGTAACTACTTCGAGCTGAG
CAGAGATCGTGGCGAGCCCGGGACGAGTTACAGTGAGCGGGATCCCGCACTCATCGCC
TGACACACAGACTCGCTCAAAAAAAAAAAAAAAAGAGTTGTAATCAAAG
GATGCCTGGGTAAGAGCTGGGTTTGGTTTGGTACTAGGTCTTTGGTAATTCCATTTAGCACCACTGAA
TATCATTAGTGCTTAAAGAGCTGCCTTTGTGGATAGAATGAATTATTATACATTCATCATTTTGTC
TTCCTACTGATACATTTAAGGAGTGGAGATACAATATTTTCATCCAATAGGTCACAATGCATATAATTGCT
GACATTT

B. Empty site Reaction of marker of Ya5ac2305:

CAAACTATCGGTATAATCTCTAATTGTCTCATTATAAAGTATTCTATTTCTATAGGACAGGTAATAATC
CAGAAAAATGAAACTAAGATGATCAAAACCTGTAGTTAATACTTTAAAATACAATCCAACACCATTTAAT
CTTCTGAGTGGTGACACTCCAATTTCTCTCTAAGGTTCCTTAAGAGTTGTAATCAAAGGATGCCTGG
GTAAGAGCTGGGTTTGGTTTGGTACTAGGTCTTTGGTAATTCCATTTAGCACCACTGAATTATCATTA
GTGCTTAAAGAGCTGCCTTTGTGGATAGAATGAATTATTATACATTCATCATTTTGTCTTCCTACTG
ATACATTTAAGGAGTGGAGATACAATATTTTCATCCAATAGGTCACAATGCATATAATTGCTGACATTT

METHOD FOR GENETIC DETECTION USING INTERSPERSED GENETIC ELEMENTS: A MULTIPLEXED DNA ANALYSIS SYSTEM

CLAIM OF PRIORITY

This application makes reference to, incorporates the same herein, and claims all benefits accruing under 35 U.S.C. § 119from an application for METHOD FOR GENETIC DETECTION USING INTERSPERSED GENETIC ELEMENTS: A MULTIPLEXED DNA ANALYSIS SYSTEM, earlier filed in the United States Patent and Trademark Office on 15 Oct. 2012 and there duly assigned Ser. No. 61/714,088.

REFERENCE TO SEQUENCE LISTING

An accompanying ASCII text file, filed via EFS-Web and including the sequence listing corresponding to this application, is hereby incorporated by reference. The sequence listing ASCII text file is named "P59855_Sequence_Listing_rev_2014.01.08.txt," was created on 8 Jan. 2014, and has a size of 28 kbytes.

BACKGROUND OF THE INVENTION

Field of the Invention

The present invention relates generally to human identification and bio-ancestry testing, and, more particularly, to improvements that enhance the sensitivity of detection during analysis of human DNA samples for human identity testing or for bio-ancestry studies.

Description of Related Art

Short tandem repeat (STR) loci are the primary genetic markers used in human identity testing. These markers are highly polymorphic and afford a high degree of sensitivity of detection such that relatively low quantities (1 ng-250 pg) of template DNA can be analyzed (Andersen, J. F., et al., *Further validation of a multiplex STR system for use in routine forensic identity testing*, Forensic Science International, 78(1): 47-64 (1996); Brinkmann, B., et al., *Mutation rate in human microsatellites: influence of the structure and length of the tandem repeat*, The American Journal of Human Genetics, 62(6): 1408-1415 (1998); Collins, P. J., et al., *Developmental validation of a single-tube Amplification of the 13 CODIS STR Loci, D2S1338, D19S433, and amelogenin: The AmpFSTR® Identifiler® PCR Amplification Kit*, Journal of Forensic Sciences, 49(6): 1265-1277 (2004); LaFountain, M. J., et al., *TWGDAM Validation of the AmpFeSTR Profiler Plus and AmpFeSTR COfiler STR Multiplex Systems Using Capillary Electrophoresis*, Journal of Forensic Sciences, 46(5): 1191-1198 (2001); Micka, K. A., et al., *Validation of multiplex polymorphic STR amplification sets developed for personal identification applications*, Journal of Forensic Sciences, 41: 582-590 (1996); Moretti, T., et al., *Validation of short tandem repeats (STRs) for forensic usage: performance testing of fluorescent multiplex STR systems and analysis of authentic and simulated forensic samples*, Journal of Forensic Sciences, 46(3): 647 (2001)).

Retrotransposable elements (REs), including long interspersed nuclear elements (LINEs), short interspersed nuclear elements (SINEs) and SVA elements, are another group of markers that can be useful for human identity testing. SINEs are a class of REs that are typically less than 500 nucleotides long; while LINEs are typically greater than 500 nucleotides long (A. F. A. Smit, *The origin of interspersed repeats in the human genome*, Current Opinion in Genetics Development, 6(6): 743-748 (1996); Batzer, M. A., et al., *Alu repeats and human genomic diversity*, Nature Reviews Genetics, 3(5): 370-379 (2002); Batzer, M. A., et al., *African origin of human-specific polymorphic Alu insertions*, Proceedings of the National Academy of Sciences, 91(25): 12288 (1994); Feng, Q., et al., *Human L1 retrotransposon encodes a conserved endonuclease required for retrotransposition*, Cell, 87(5): 905-916 (1996); Houck, C. M., et al., *A ubiquitous family of repeated DNA sequences in the human genome*, Journal of Molecular Biology, 132(3): 289-306 (1979); Kazazian, H. H., et al., *The impact of L1 retrotransposons on the human genome*, Nature Genetics, 19(1): 19-24 (1998); Ostertag, E. M., et al., *Biology of mammalian L1 retrotransposons*, Annual Review of Genetics, 35(1): 501-538 (2001)). LINE full-length elements are ~6 kb in length, contain an internal promoter for polymerase and two open reading frames (ORFs) and end in a polyA-tail. SINEs include Alu elements, primate specific SINEs that have reached a copy number in excess of one million in the human genome. SINEs were originally defined by their interspersed nature and length (75-500 bp), but have been further characterized by their RNA polymerase III transcription. The third type of RE is the composite retrotransposon known as an SVA (SINE/VNTR/Alu) element (Wang, H., et al., *SVA Elements: A Hominid-specific Retroposon Family*, J. Mol. Biol. 354: 994-1007 (2005)). SVAs are composite elements named after their main components, SINE, a variable number of tandem repeats (VNTR), and Alu. As a consequence of the VNTR region, full-length SVA elements can vary greatly in size. These markers have potential application to identity testing, kinship analyses, and evolutionary studies (see Smit; Batzer, et al. (2002); Batzer, et al. (1994); Feng, et al.; Houck, et al.; Kazazian et al.; and Ostertag, et al., references, cited supra). Insertion and null allele (INNUL) markers may include SINEs, LINEs and SVAs.

The structure of REs is described in FIG. 1. The Alu family of interspersed repeats is the most successful of the mobile genetic elements within primate genomes, having amplified to a copy number of greater than 500,000 per haploid genome. Alu elements mobilize via an RNA polymerase III-derived intermediate in a process defined as retroposition. Alu repeats are approximately 300 bp in length and are ancestrally derived from the 7SL RNA gene. Each Alu element is dimeric in structure and is flanked by short intact direct repeats. These direct repeat sequences are formed when an Alu element inserts within staggered nicks in the genome. In addition, each Alu element has an oligo dA-rich region in the middle and at the 3' end (FIG. 1). The amplification of Alu repeats to such large copy numbers has occurred over a period of 65 million years and the process is still active in the present day genome (A. F. A. Smit, *The origin of interspersed repeats in the human genome*, Current Opinion in Genetics Development, 6(6): 743-748 (1996); Zangenberg, et al., cited supra; Budowle, B., *SNP typing strategies*, Forensic Science International, 146: S139 (2004)).

Alu sequences within the human genome can be divided into subfamilies of related members based upon the presence of diagnostic mutations shared in common by subfamily members. These subfamilies are of different evolutionary ages with the younger ones (Ya5, Ya8 and Yb8) being primarily restricted to the human genome (Houck, C. M., et al., *A ubiquitous family of repeated DNA sequences in the human genome*, Journal of Molecular Biology, 132(3): 289-306 (1979); Kazazian, H. H., et al., *The impact of L1*

*retrotransposons on the human genome*, Nature Genetics, 19(1): 19-24 (1998)). These subfamilies arose in a hierarchical manner over evolutionary time with the younger subfamily members retaining the diagnostic mutations of the older subfamily that preceded it.

The Ya5/8 and the Yb8 subfamilies are independent derivatives of the Y subfamily of Alu repeats. The young subfamilies are present in relatively small copy numbers within the genome compared to the bulk of the Alu repeats, which primarily belong to the PS and AS subfamilies. For instance, the Y subfamily is comprised of approximately 100,000 members; Ya5 subfamily, 1000 members; Ya8 subfamily, 50 members and the Yb8 subfamily, approximately 1000 members (Moretti, T., et al., *Validation of short tandem repeats (STRs) for forensic usage: performance testing of fluorescent multiplex STR systems and analysis of authentic and simulated forensic samples*, Journal of Forensic Sciences, 46(3): 647 (2001)).

The youngest subfamilies of Alu elements, Ya5, Ya8 and Yb8 first arose in the primate genomes approximately 5 million years ago (Batzer, M. A., et al., *African origin of human-specific polymorphic Alu insertions*, Proceedings of the National Academy of Sciences, 91(25): 12288 (1994); Feng, Q., et al., *Human L1 retrotransposon encodes a conserved endonuclease required for retrotransposition*, Cell, 87(5): 905-916 (1996)). Amplification of Alu elements within humans is still an ongoing process. As human population groups migrated and colonized different parts of the world, all new Alu insertions in individuals belonging to the newer populations were absent in the original population, and vice versa. In other words, several elements that belong to the young subfamilies are dimorphic for their presence/absence within different human population groups (Syvanen, A. C., et al., *Identification of individuals by analysis of biallelic DNA markers, using PCR and solid-phase minisequencing*, American Journal of Human Genetics, 52(1): 46-59 (1993); LaRue, B. L., et al., *A validation study of the Qiagen Investigator DIPplex® kit; an INDEL-based assay for human identification*, International Journal of Legal Medicine, 2012, 1-8).

Realizing the potential of these dimorphic Alu elements as genetic markers, investigators have identified the dimorphic Alu repeats from a larger background of fixed Alu elements. Using the Alu insertion PCR assay described in FIG. 2, each Alu element was tested against a panel of several human genomic DNA samples as templates for the levels of polymorphism. Each and every dimorphic Alu repeat has been thoroughly characterized for its respective allele frequency in as many as 50 different worldwide population groups (Syvanen, A. C., et al., *Identification of individuals by analysis of biallelic DNA markers, using PCR and solid-phase minisequencing*, American Journal of Human Genetics, 52(1): 46-59 (1993); LaRue, B. L., et al., referenced supra; Shriver, M. D., et al., *Ethnic-affiliation estimation by use of population-specific DNA markers*, American Journal of Human Genetics, 60(4): 957 (1997)).

Ustyugova, S. V., et al. (*Cell line fingerprinting using retroelement insertion polymorphism*. BioTechniques, 38(4): 561-565 (2005)), demonstrated that REs could be used for cell line identification. Novick, et al. (*Polymorphic human specific Alu insertions as markers for human identification*. Electrophoresis, 16(1): 1596-1601 (1995)), and Mamedov, et al. (*A new set of markers for human identification based on 32 polymorphic Alu insertions*, European Journal of Human Genetics, 18(7): 808-814 (2010)), recently described a set of Alu's (a type of SINE) for paternity testing. Both of these studies intimated that the systems could be applied to forensic analyses. The REs have low mutation rates which makes them appealing for kinship analyses compared with the less stable STRs. In addition, they do not yield stutter artifacts, due to slippage during the PCR, which can reduce some interpretation issues associated with STRs in forensic mixture profiles (Andersen, J. F., et al., *Further validation of a multiplex STR system for use in routine forensic identity testing*, Forensic Science International, 78(1): 47-64 (1996); Brinkmann, B., et al., *Mutation rate in human microsatellites: influence of the structure and length of the tandem repeat*, The American Journal of Human Genetics, 62(6): 1408-1415 (1998); Moretti, T., et al., *Validation of short tandem repeats (STRs) for forensic usage: performance testing of fluorescent multiplex STR systems and analysis of authentic and simulated forensic samples*, Journal of Forensic Sciences, 46(3): 647 (2001)).

Forensic samples often are compromised in quality and quantity. Degraded samples may contain fragments of DNA that are less than 250 bp in length, and the quantities may be limited to subnanogram levels of recoverable DNA (Burger, J., et al., *DNA preservation: A microsatellite DNA study on ancient skeletal remains*, Electrophoresis, 20(8): 1722-1728 (1999); Fondevila, M., et al., *Challenging DNA: assessment of a range of genotyping approaches for highly degraded forensic samples*, Forensic Science International: Genetics Supplement Series, 1(1): 26-28 (2008); Golenberg, E. M., et al., *Effect of Highly Fragmented DNA on PCR*, Nucleic Acids Research, 24(24): 5026-5033 (1996); R. Hughes-Stamm, S., et al., *Assessment of DNA degradation and the genotyping success of highly degraded samples*, International Journal of Legal Medicine, 125(3): 341-348 (2011)). REs can range in size from hundreds (SINEs) to several thousand (LINEs) by in length (see Smit; Batzer, et al. (2002); Batzer, et al. (1994); Feng, et al.; Houck, et al.; Kazazian et al.; and Ostertag, et al., references, cited supra). Previous attempts to use Alu sequences for identity testing capitalized on the size difference between insertion and null alleles by amplifying the entire region with the same forward and reverse primers (Novick, G. E., et al., *Polymorphic human specific Alu insertions as markers for human identification*, Electrophoresis, 16(1): 1596-1601 (1995)). The insertion allele would be 200-400 bp larger than the null allele, and could be detected electrophoretically based on size differences. While useful for paternity testing and some population studies where DNA quality is not compromised, the large size difference between amplicons of the null and insertion alleles will impact amplification efficiency during the PCR and is a limitation for forensic samples. The limitation is differential amplification favoring the smaller amplicon (i.e., the null allele) and possibly dropping out of the insertion element, which is exacerbated if the sample is highly degraded.

The use of SINEs such as Alu repeats in determining human identity has been studied and reported (see Mamedov, et al., and Novick, et al., cited supra). Until now, however, due to the inherent size difference associated with INNULs, the use of REs has not been useful in a practical sense. Although REs make up over 40% of the human genome (Lander, E. S., et al., *Initial sequencing and analysis of the human genome*, Nature, 409(6822): 860-921 (2001)) and present myriad potential targets for human identity testing, these INNULS (i.e., insertion and null alleles, instead of INDELs because one of the allele forms is not the result of a deletion) have received limited attention for use in forensic human identity testing (Zangenberg, et al., *Multiplex PCR: Optimization Guidelines*, in PCR Applications:

Protocols for Functional Genomics, Academic Press, San Diego, Calif., 1999, p. 73-94).

Advantageously, a convenient way to design synthetic primers for PCR amplification of relatively short, repeating sequences, known as the mini-primer design, has been previously described in U.S. Pat. No. 7,794,983 B2, to Sinha, et al., which is hereby incorporated by reference. Using the mini-primer design, interspersed genetic elements containing characteristic direct repeat sequences (direct repeats) may be amplified and quantitated.

The above information disclosed in this Background section is only for enhancement of understanding of the background of the invention, and, therefore, it may contain information that does not form the prior art that is already known to a person of ordinary skill in the art.

SUMMARY OF THE INVENTION

Accordingly, one object of the present invention is to provide, using the mini-primer design, synthetic primers for Interspersed Element Insertion polymorphisms that would facilitate the production of small PCR products having as few as 50 to 150 base pairs (bp) when human genomic DNA is amplified.

This short sequence PCR amplification process takes advantage of the fact that all retrotransposon insertions have a characteristic sequence at the beginning and the end of insertion referred as Target Site Duplication (TSD). Another object of the present invention is to design synthetic primers to include part or full TSD sequences to provide specific insertion or no-insertion alleles in multiplex systems.

Another object of the present invention is to design, optimize and validate a multiplex amplification system (single amplification for multiple targets) containing LINEs, SINEs and SVAs for forensic applications.

Another object of the present invention is to design, optimize and validate a multiplex amplification system (single amplification for multiple targets) containing LINEs, SINEs and SVAs for bio-ancestry applications.

Another object of the present invention is to use the power of discrimination and analytical performance of the short sequence PCR amplification process to select markers as being suitable for either forensic or bio-ancestry applications.

Another object of the present invention is to develop a practical method for using LINEs and SVAs as potential markers in a DNA amplification system for human identification.

Another object of the present invention is to develop a multiplex amplification system that makes use of RE markers and is useful in forensic cases in which the DNA samples have been substantially degraded.

These and other objects may be attained by utilizing the mini-primer strategy with INNUL markers, which include SINEs, LINEs, and SVAs and can be effectively used as markers for human identification and bio-ancestry studies regardless of the size of the inserted element. The size of the amplicons for INNULs and the difference between allelic states can be reduced substantially such that these markers have utility for analyzing high and low quality human DNA samples. In addition, the present invention demonstrates a sensitivity of detection that can be sufficient to enable human identity and bio-ancestry studies on forensic and anthropological samples. Depending on the markers selected and the distribution of the alleles in global populations, INNULs can be selected for human identity testing or for bio-ancestry studies.

The optimization of INNUL markers into a single-tube, multi-locus reaction furthers these goals. The inclusion of these markers in a multiplexed reaction produces an INNUL-based human identity test set that is a powerful tool for use in forensic settings without the need for further investment in new instrumentation. The multiplexed system is able to amplify multiple target sequences at the same time with no non-specific amplification products and also exhibits the sensitivity to amplify DNA concentration as low as 100 pg or less. With a size range of 46-124 base pairs, this novel multiplexed system contains the smallest size amplicons that are both amenable for use with extensively degraded DNA samples and available to the forensic community. Thus, the INNUL multiplex system of the present invention provides a statistically discriminating tool that is useful for forensic applications where the sample is limited in quantity as well as quality.

One embodiment of the present invention includes a method for genetic detection comprising providing a sample to be analyzed, selecting a plurality of Retrotransposable element (RE) markers, each selected RE marker being an INNUL marker that is associated with both a filled allele representing a filled genomic site and an empty allele representing an empty genomic site, each INNUL marker comprising a nucleic acid sequence, the nucleic acid sequence being found at a location within the genome of a target species, providing a primer set corresponding to each selected INNUL marker, each primer set consisting of a forward primer and two reverse primers, the two reverse primers consisting of a primer corresponding to a filled site of the INNUL marker and a primer corresponding to an empty site of the INNUL marker, combining the primer sets with the sample to form a reaction mixture, amplifying the markers using the primer sets to form a mixture of amplification products, separating the amplification products from the remainder of the reaction mixture, and detecting and quantitating each labeled amplification product.

In certain embodiments of the present invention, each forward primer used in the above method may have a structure comprising an observable label. In certain embodiments, each reverse primer used in the above method may have a structure comprising an observable label.

In certain embodiments of the present invention, each forward primer used in the above method may have a structure comprising a fluorescent organic dye. In certain embodiments, each reverse primer used in the above method may have a structure comprising a fluorescent organic dye.

In certain embodiments of the present invention, the observable labels may be selected from 6-carboxyfluorescein (sold as 6-FAM), 6-carboxy-4',5'-dichloro-2'7'-dimethoxyfluorescein (sold as JOE), 6-carboxytetramethylthodamine (sold as TAMRA) and 6-carboxy-X-rhodamine (sold as ROX).

In certain embodiments of the present invention, amplification of the markers may be done using a real-time polymerase chain reaction (PCR) system.

In certain embodiments of the present invention, each amplification product may be labeled with a distinct observable label.

In certain embodiments of the present invention, each primer set may correspond to a PCR amplicon corresponding to a filled allele and a PCR amplicon corresponding to an empty allele, and each PCR amplicon may have a size of from about 46 base pairs to about 200 base pairs.

In certain embodiments of the present invention, the selected INNUL markers may be selected from SINEs, LINEs and SVAs.

In certain embodiments of the present invention, the selected INNUL markers may be selected from Alus and LINEs.

In some embodiments of the present invention, the set of INNUL markers used may be selected for human identity testing purposes on the basis of the distribution of the alleles in global populations.

In some embodiments of the present invention, the set of INNUL markers used may be selected for bio-ancestry studies on the basis of the distribution of the alleles in global populations.

In certain embodiments of the present invention, useful forensic or bio-ancestry-related determinations may be obtained for samples comprising as little as 100 pg of DNA.

In certain embodiments of the present invention, each selected INNUL marker comprises a Target Site Duplication (TSD) sequence, also referred to as a direct repeat sequence, and each reverse primer comprises a nucleic acid sequence that includes all or part of the TSD sequence.

In certain embodiments of the present invention, the genetic detection method may include INNUL markers selected from CHR20-79712, Ya5-MLS48, Yb8NBC13, Ya5ACA1736, Yb8NBC106, Y5ac2305, HS4.69, AC4027, CH1-6217, Yb8AC1796, Yac52265, MLS9, TARBP1, SVA306, Amelogenin, SVA323, Ya5NBC51, Yb8AC1141, Yb7AD155 and Ya5-MLS18. In one embodiment, a multiplex system for genetic detection may comprise the amplification of filled and empty amplicons corresponding to each of these fifteen INNUL markers plus Amelogenin.

In certain embodiments of the present invention, the reaction products may be separated from the remainder of the PCR reaction mixture and from each other using electrophoresis.

In certain embodiments of the present invention, each INNUL marker may comprise a filled allele and an empty allele, and the size difference between each filled allele and the corresponding empty allele may be in the range of from about 2 to about 8 base pairs.

Embodiments of the present invention may include a multiplexed DNA analysis system comprising a sample of DNA, a set of thirty or fewer INNUL markers, each INNUL marker comprising a filled allele and an empty allele, a set of three primers corresponding to each INNUL marker, each set of primers including a forward primer and two reverse primers, the forward primer including a detectable label, one reverse primer corresponding to the filled allele and the other reverse primer corresponding to the empty allele, a polymerase chain reaction (PCR) amplification system that produces PCR amplification products, means for separating PCR amplification products from reactants and from each other, means for detecting and quantitating PCR amplification products using the detectable label, and means for deriving a useful forensic-related or bioancestry-related conclusion from the quantitative PCR results.

In certain embodiments of the present invention, the separating means of the multiplexed DNA analysis system may be electrophoresis.

In certain embodiments of the present invention, the multiplexed DNA analysis system may be based on amplification of a set of 15 INNUL allele markers plus Amelogenin.

In certain embodiments; of the present invention, the multiplexed DNA analysis system may include forward primers that are labeled with fluorescent organic dyes. In some embodiments, the fluorescent organic dyes may be selected from the group of four dyes consisting of 6-carboxyfluorescein (sold as 6-FAM), 6-carboxy-4',5'-dichloro-2'7'-dimethoxyfluorescein (sold as JOE), 6-carboxytetramethylrhodamine(sold as TAMRA), and 6-carboxy-X-rhodamine (sold as ROX).

In certain embodiments of the present invention, the amplification products of the above methods and systems may be characterized by Next Generation Sequence analysis (NGS) methods.

In certain embodiments of the present invention, the amplification products of the above methods and systems may be characterized by rapid DNA analysis platforms.

BRIEF DESCRIPTION OF THE FIGURES

The patent or application file contains at least one drawing executed in color. Copies of this patent or patent application publication with color drawing(s) will be provided by the Office upon request and payment of the necessary fee.

A more complete appreciation of the invention, and many of the attendant advantages thereof, will be readily apparent as the same becomes better understood by reference to the following detailed description when considered in conjunction with the accompanying figures, wherein.

The Alu sequence is represented by the shaded line. The chromosomal locus harboring the Alu element is represented by the thick dark line, and the flanking unique sequence derived PCR primers are denoted by the arrows.

The PCR assay results in the production of approximately a 100 bp or a 400 bp DNA fragment or both as outlined in the figure. Individuals that are homozygous for the Alu insertion will amplify only 400 bp fragment (#1), while those that are homozygous for the absence of Alu insertion at this locus will amplify only a 100 bp fragment (#3). Individuals heterozygous for the Alu insertion will amplify both the 400 bp and 100 bp fragments (#2).

FIG. 3 illustrates primer design sequences for the filled (SEQ ID NO: 81) and empty (SEQ ID NO: 82) sites of RE marker Ya5ac2305. The primer sequences for mini-primer design are underlined. The traditional "core primer" design sequences, as reported earlier, are in bold and italics. The forward primer is identical in both sites. The uniqueness for each site lies within the reverse primer sequences. In the Filled Site reaction (A), the reverse primer contains the direct repeat sequence (red box), flanking genomic sequence and some of the 5' Alu insert sequence. Empty Site reaction (B) reverse primer contains the whole direct repeat plus flanking genomic sequence.

Figure 1:
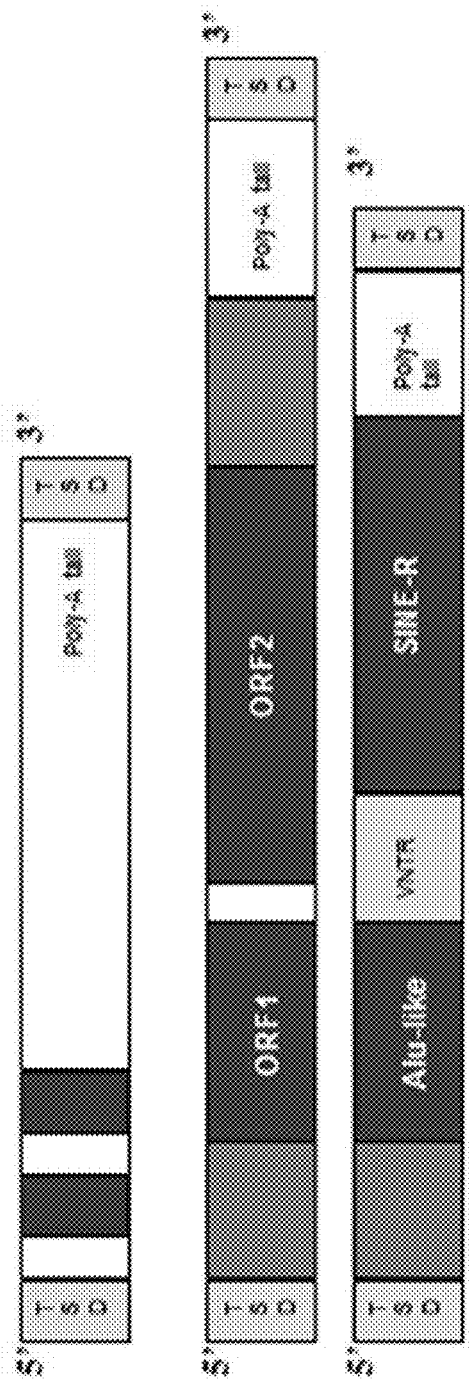
FIG. 1 illustrates Alu, L1 and WA. Full-length retrotransposons are not drawn to scale. As represented, all three REs have at the beginning and end a target site duplication (TSD) consisting of identical DNA sequences. The mini primer design strategy exploits these TS Ds for amplification and detection of insertion or null alleles.
Figure 2:
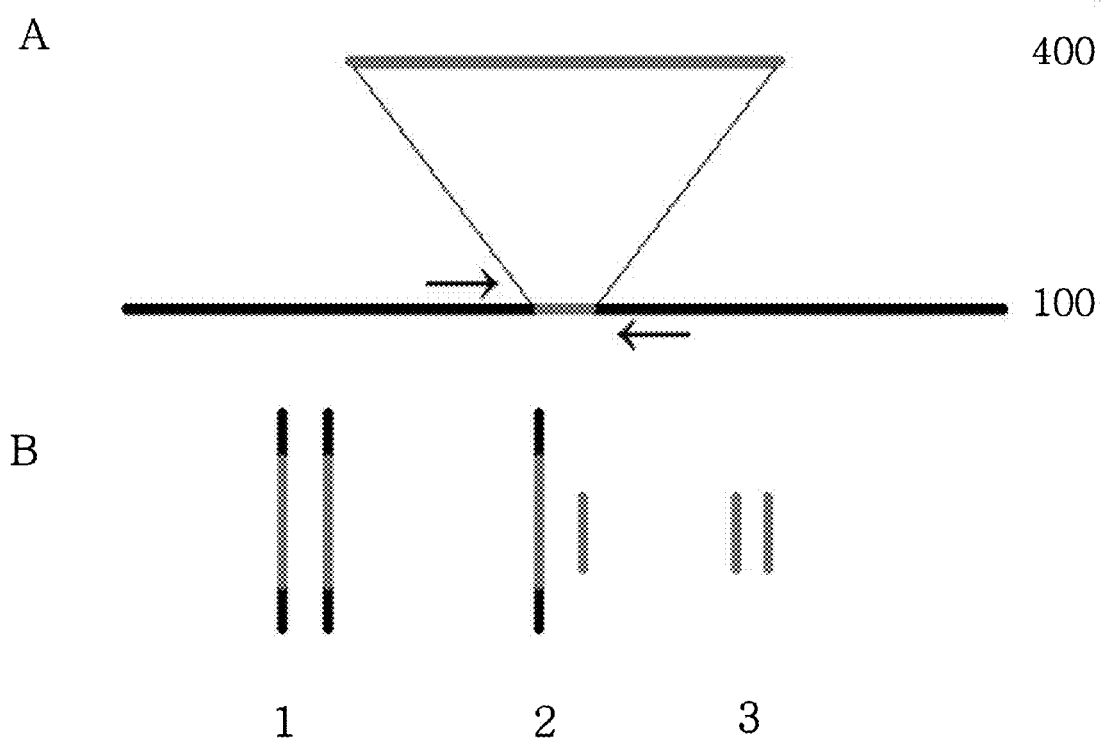
FIG. 2 illustrates the schematic of the Alu element insert on PCR assay.
Figure 4:
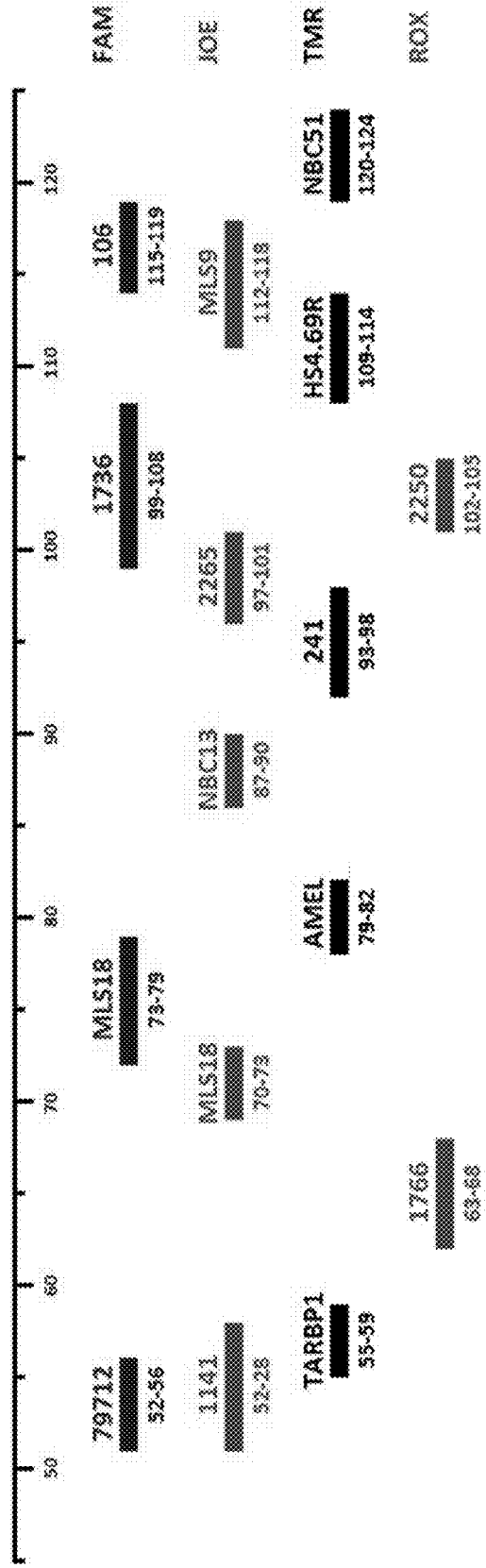

FIG. 4 illustrates a multiplex design showing markers, dyes, and amplicon sizes for each locus.

Figure 5:
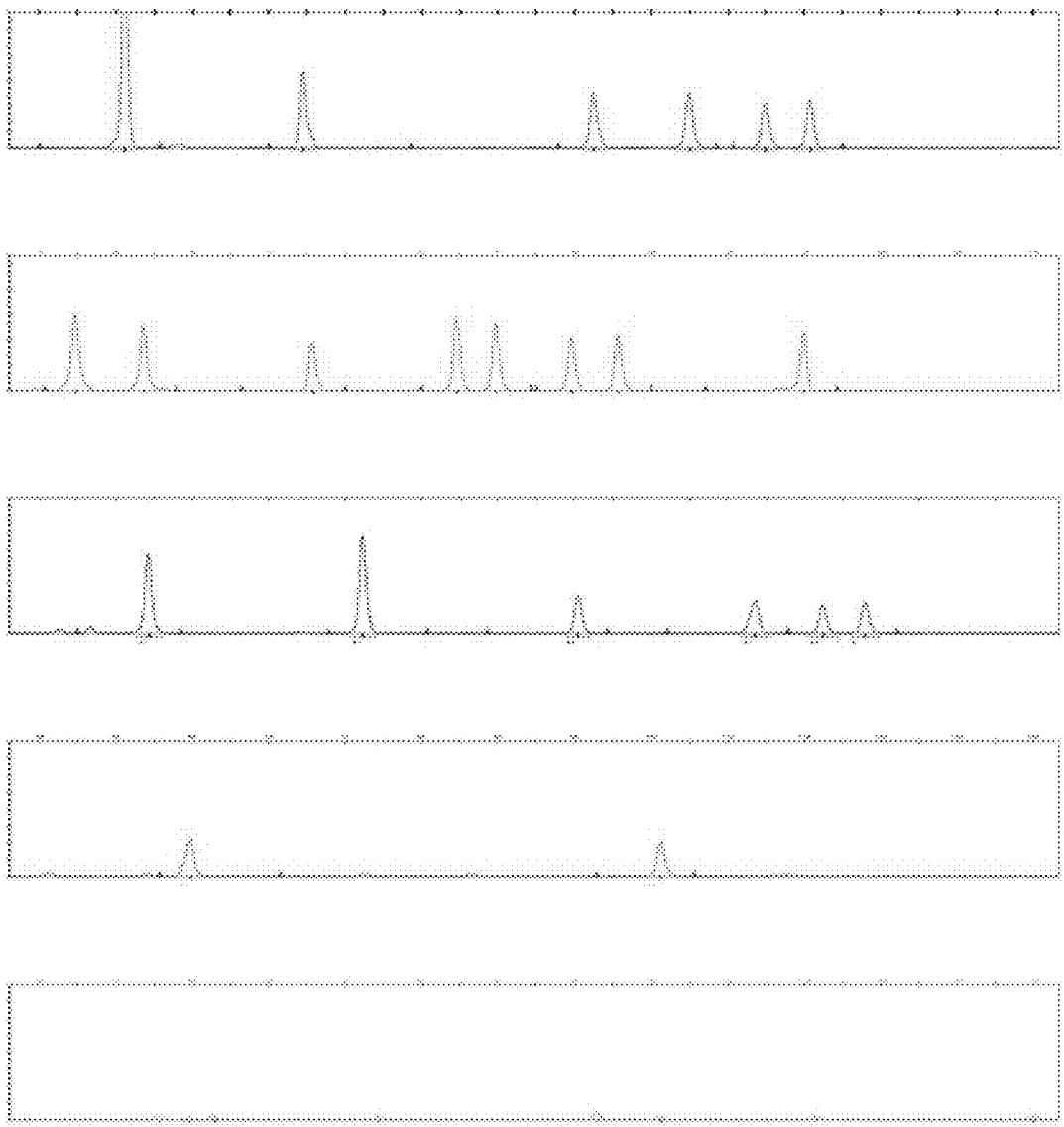

FIG. 5 illustrates an electropherogram representing 15 RE markers and Amelogenin multiplexed using five fluorophores: 6-carboxyfluorescein (blue), 6-carboxy-4',5'-dichloro-2',7'-dimethoxyfluorescein (green), 6-carboxytetramethylrhodamine, (black but represents yellow), 5/6-carboxy-X-rhodamine (red), and CC5 (orange fluorophore proprietary to Promega) as the size standard using 3130 Genetic Analyzer (Applied Biosystems). The fluorophores may be represented as 6-carboxyfluorescein (sold as 6-FAM) 1, 6-carboxy-4',5'-dichloro-2',7'-dimethoxyfluorescein (sold as JOE) 2, 6-carboxytetramethylrhodamine (sold as TAMRA) 3, or 6-carboxy-X-rhodamine (sold as ROX) 4. ROX may be a mixture of the 6-carboxy- isomer 4 and the 5-carboxy- isomer 5. The "X" groups are "linker" groups that connect an oligonucleotide to a dye label. As is well known in the art, various amide or other groups may be used as linkers.

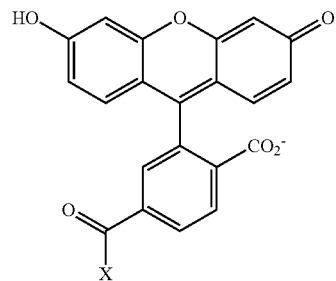

1

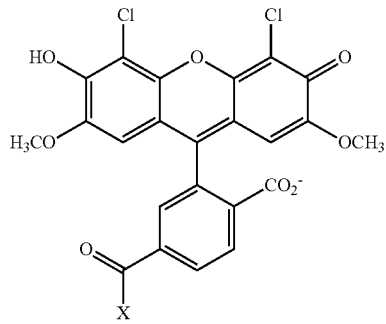

2

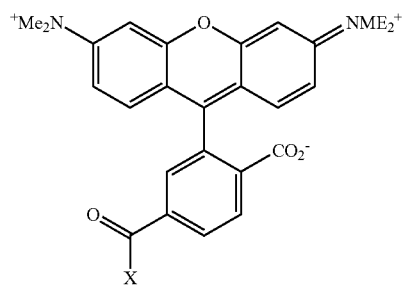

3

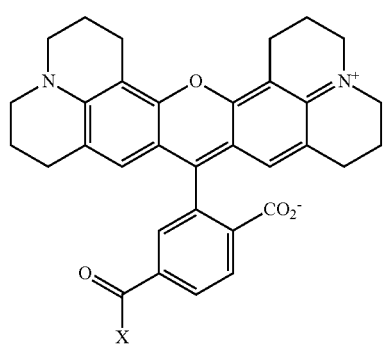

4

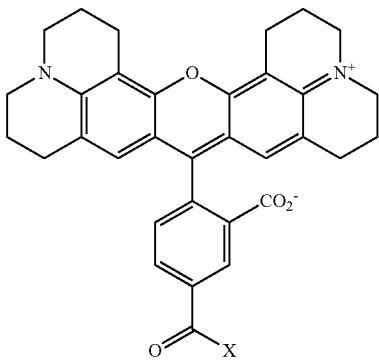

5

Figure 6:
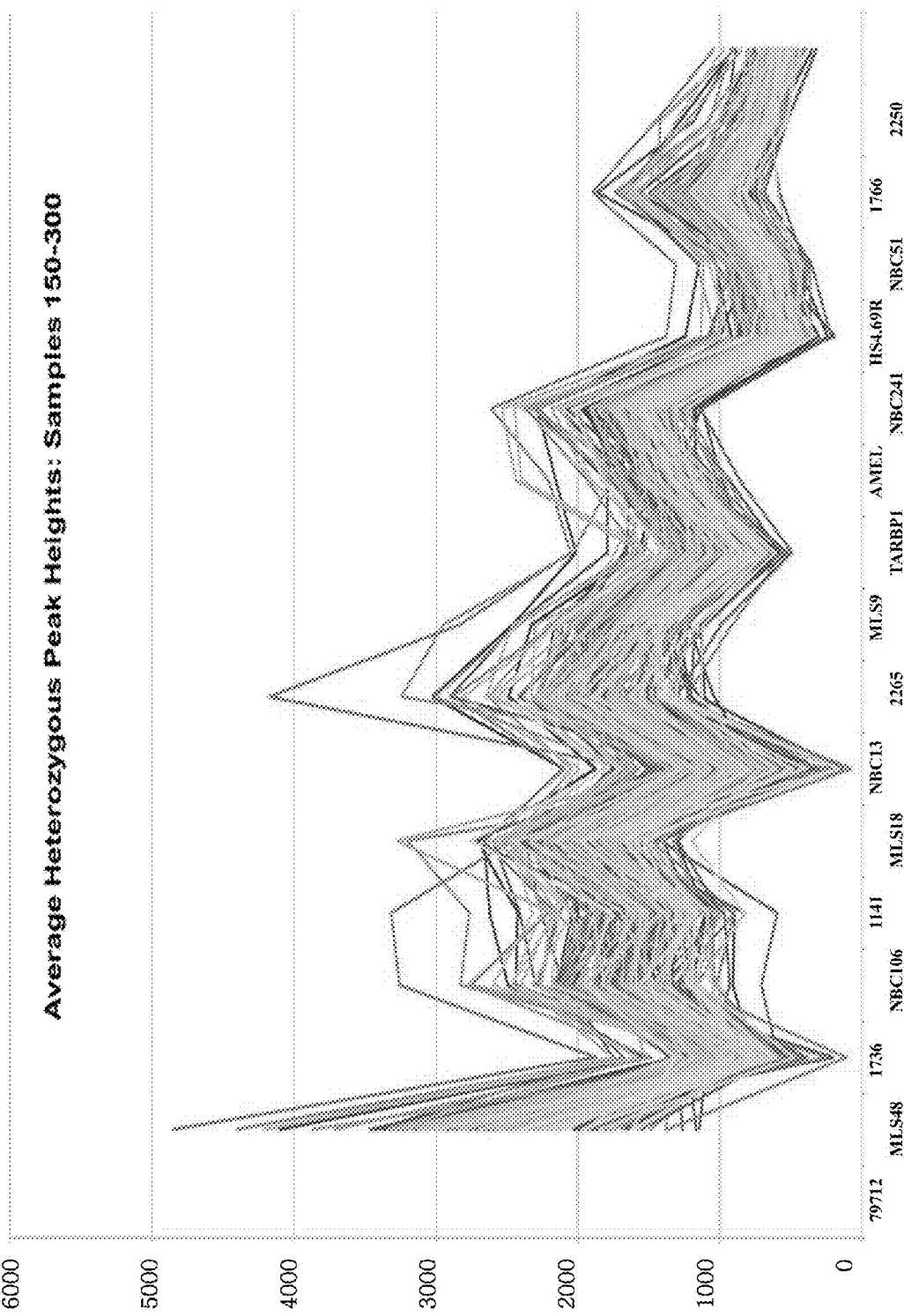

FIG. 6 illustrates average heterozygous peak heights for 150 database samples. RFU vs. Marker.

Figure 7:
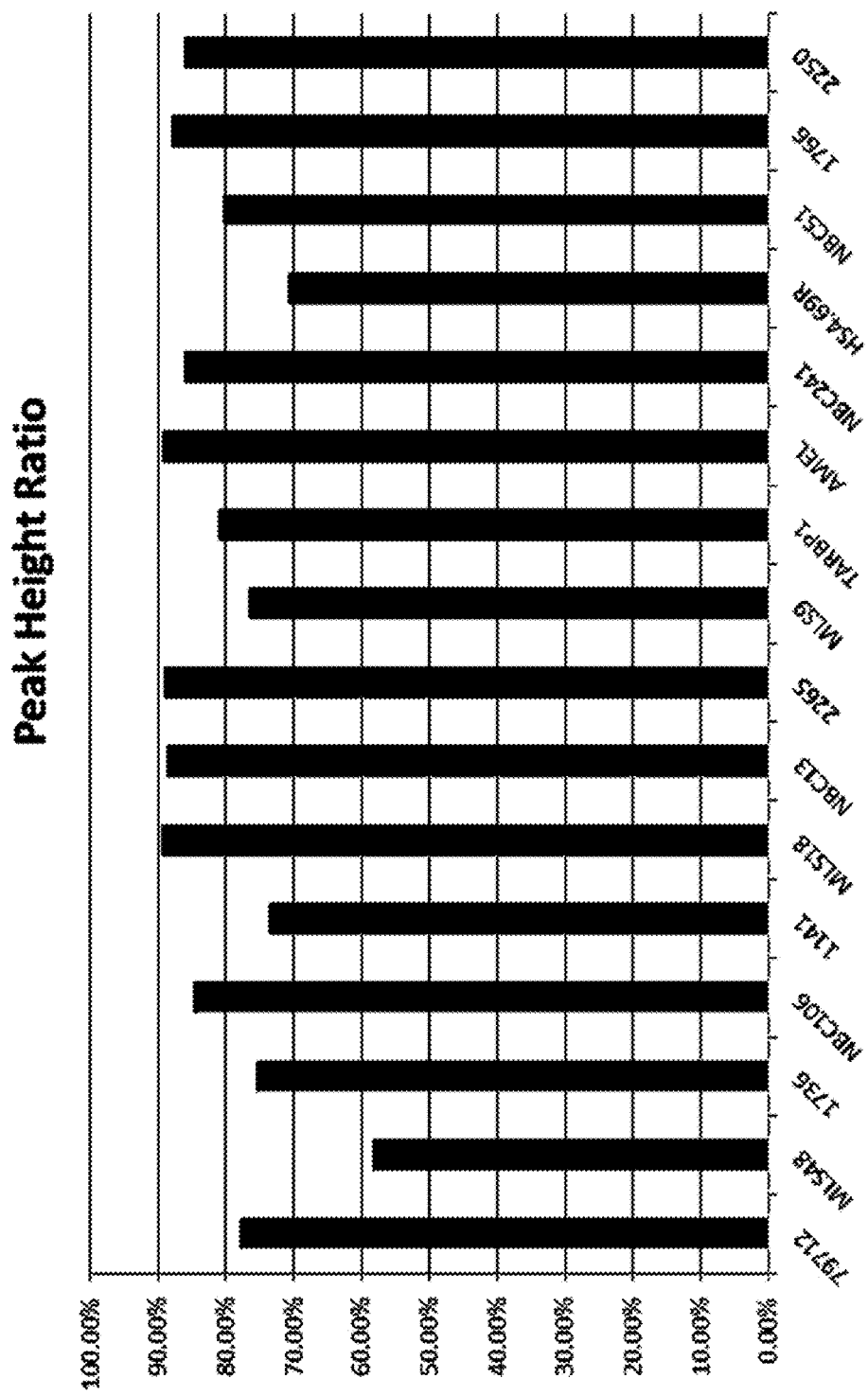

FIG. 7 illustrates a heterozygosity of database samples.

Figure 8:
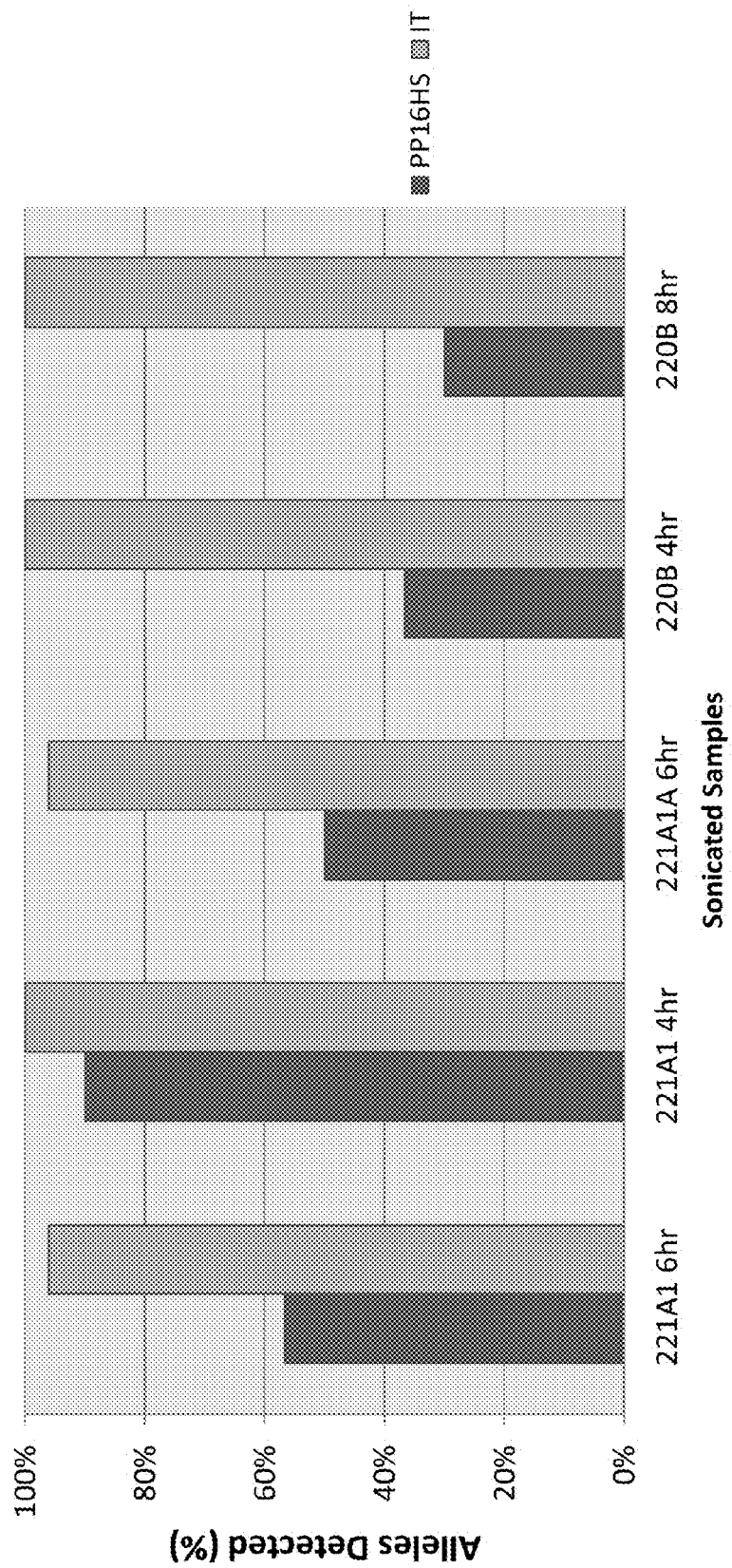

FIG. 8 illustrates the multiplex DNA typing system sold by Promega as PowerPlex® 16HS (PP16HS) vs. the small amplicon DNA typing system offered by InnoGenomics as InnoTyper™ (IT). Results confirmed that InnoTyper™ was two times more sensitive in number of alleles detected.

Figure 9:
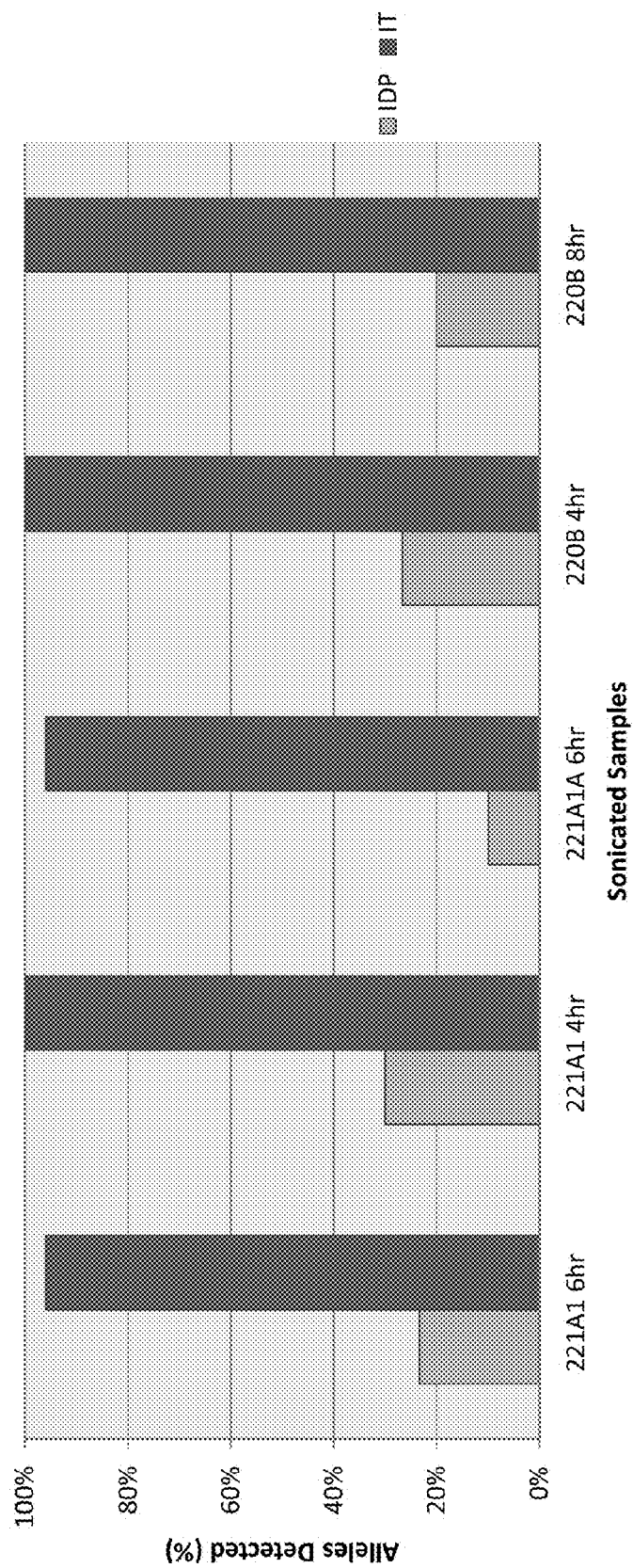

FIG. 9 illustrates the multiplex DNA amplification kit sold by Life Technologies as Identifiler® Plus (IDP) vs. the small amplicon DNA typing system offered by InnoGenomics as InnoTyper™ (IT). Results confirmed that InnoTyper™ was four times more sensitive in number of alleles detected.

Figure 10:
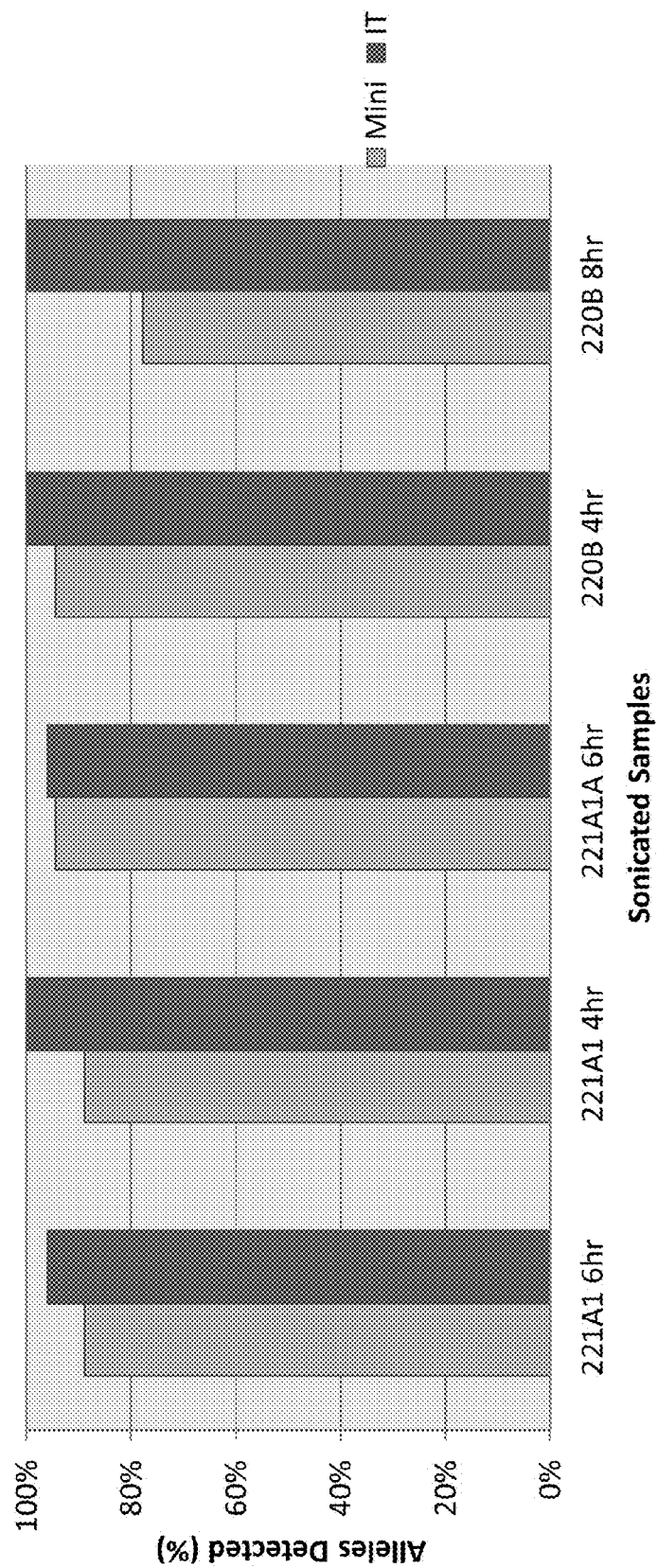

FIG. 10 illustrates the multiplex DNA amplification kit sold by Life Technologies as Minifiler Plus™ (Mini) vs. the small amplicon DNA typing system offered by InnoGenomics as InnoTyper™ (IT) multiplex. Results confirmed that InnoTyper™ was ten percent more sensitive in number of alleles detected.

Figure 11:
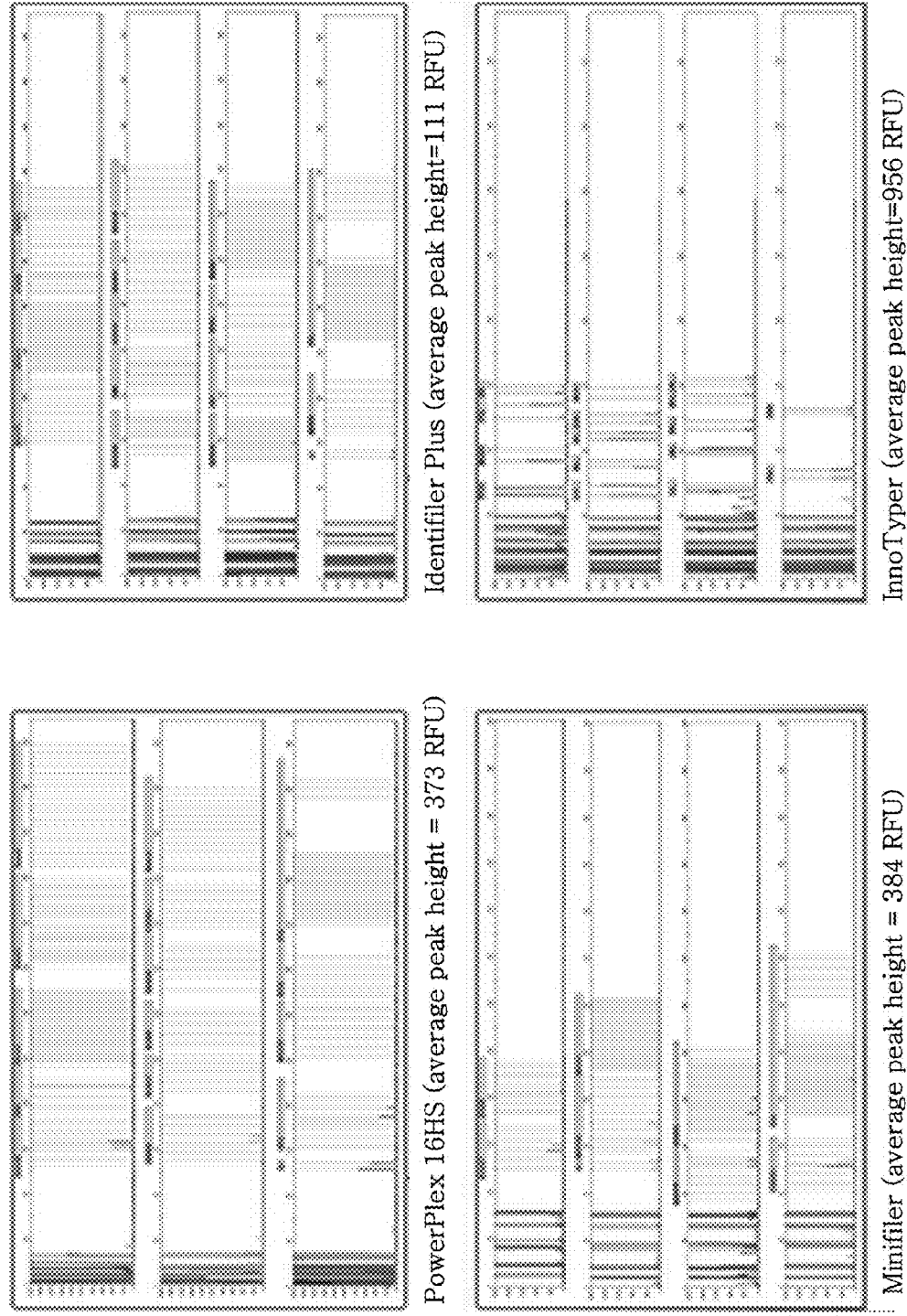

FIG. 11 illustrates a comparison of degraded DNA profiles using STR DNA typing kits PowerPlex® 16 HS, Indentifiler Plus™, Minifiler™ and InnoTyper™ multiplex.

Figure 12:
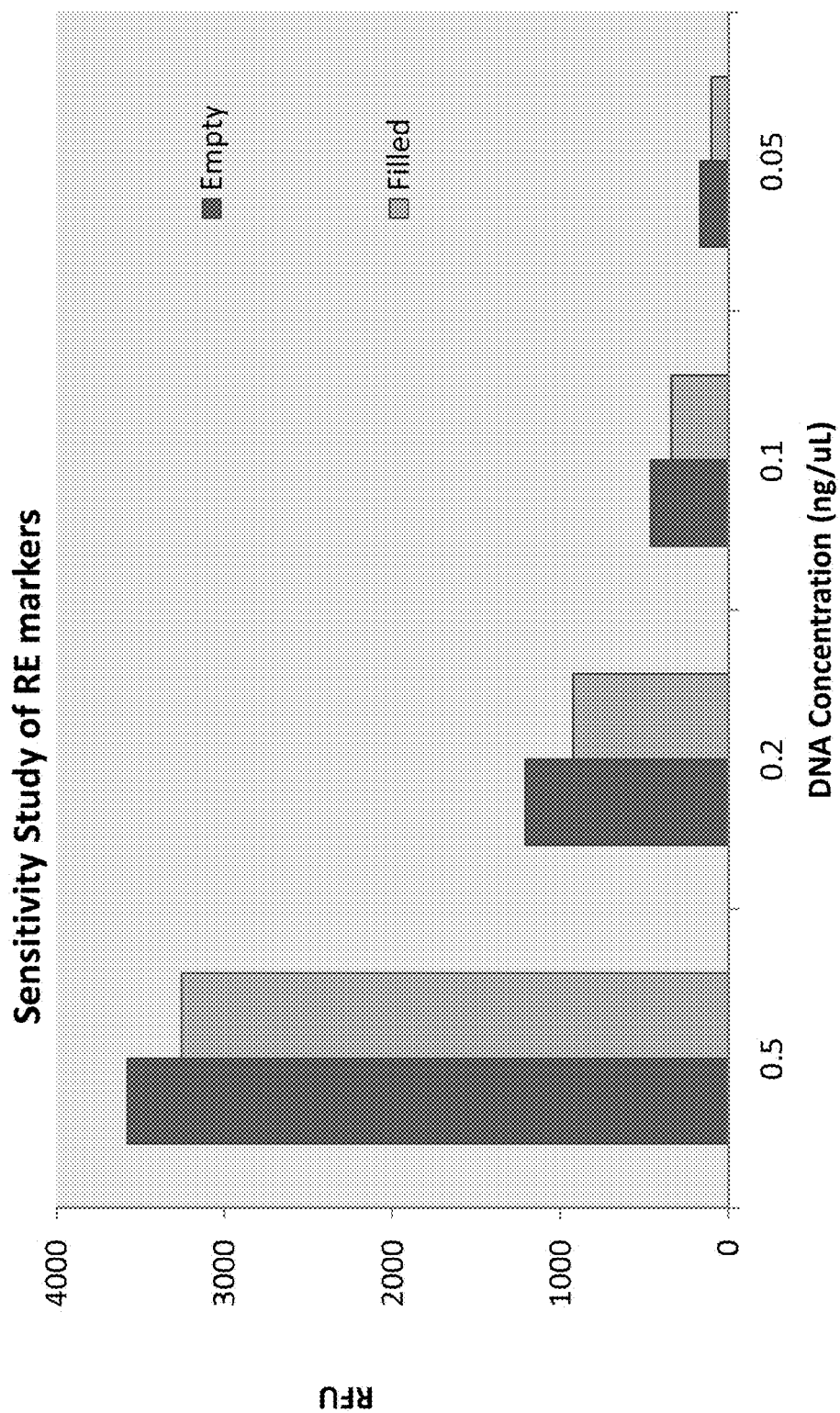

FIG. 12 illustrates a sensitivity study of markers showing the average peak height of empty and filled primers at varying concentrations of DNA (0.5-0.05 ng/μL). Empty results showed slightly higher peak intensities than Filled results.

Figure 13:
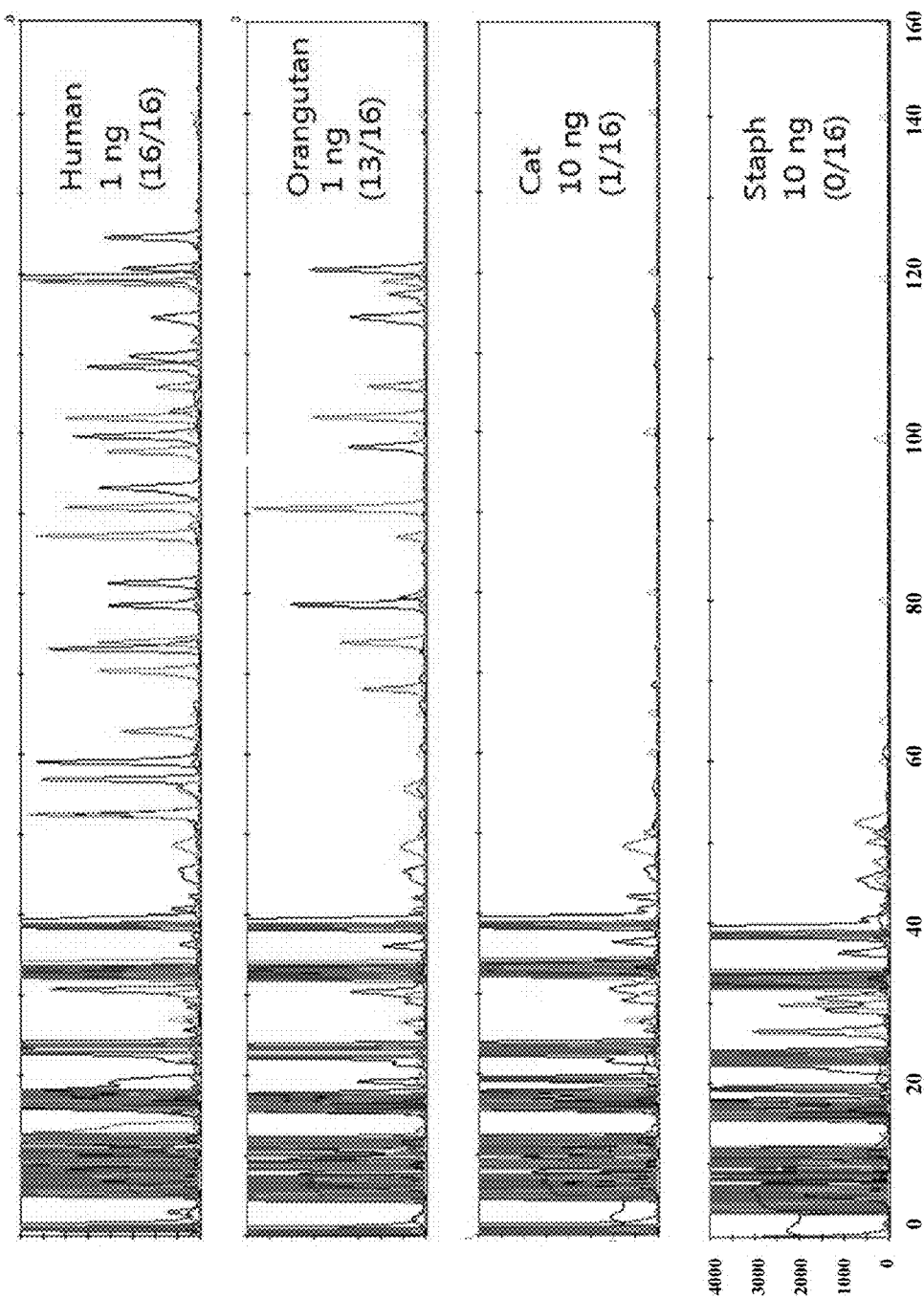

FIG. 13 illustrates species results generated by the small amplicon DNA typing system offered by InnoGenomics as InnoTyper™.

DETAILED DESCRIPTION OF THE INVENTION

Embodiments of the present invention provide for the first time for the use of LINEs, SINEs, or SVA element insertions for forensic applications. One object of the present invention is to design and obtain synthetic primers based on the mini-primer design (see U.S. Pat. No. 7,794,983 B2, to Sinha, et al.) for Interspersed Element Insertion polymorphisms that would produce small PCR products that include as few as 50 to 150 base pairs (bp) when human genomic DNA is amplified. All retrotransposon insertion has a characteristic sequence that appears at the beginning and again at the end of insertion, and this is referred to as Target Site Duplication (TSD). One embodiment of the present invention includes the design of synthetic primers to include a part or full TSD sequence in order to quantitate specific insertion or no-insertion alleles using a multiplex system. In another embodiment of the present invention, based on the power of discrimination and analytical performance, markers were selected and chosen as suitable for either forensic or bio-ancestry applications. Another embodiment of the present invention provides for the design, optimization and validation of a multiplex amplification system (single amplification for multiple targets) containing LINEs, SINEs, and SVAs for forensic applications.

In addition to developing a practical method for using SINEs for genotyping individuals, the present invention demonstrates for the first time that LINEs and SVAs can be used as potential markers for human identification. Fifteen forensically suitable markers were selected to include in a 4-dye multiplex system. Among the 15 markers (including LINEs and Alu), the amplicon sizes ranged between 46 and 124 bp. A population study using 51 Caucasian and 51 African American samples was performed using 11 fluorescently labeled primer sets. The same 102 samples were analyzed with STR and compared with the RE results by a statistician. The data indicated that the RE markers are statistically independent of STR loci as well as among themselves. This statistical independence is critically important in establishing the validity of the use of RE markers for the forensic evaluation of DNA. The total power of discrimination for the combination of only these 11 markers was greater than 1 in 1000s for the Caucasian population and almost 10 fold more, greater than 1 in 10,000, for the African American population. The ability to discriminate among samples will only increase with the addition of more loci.

A degradation study was performed to assess the performance of RE markers on compromised samples, such as those encountered in forensic cases. Results demonstrate that the system is successful in obtaining meaningful results from highly degraded DNA.

A sensitivity study was performed to establish the minimum DNA quantity from which results can accurately be obtained. This study has demonstrated that bi-allelic INNULs in the range of 46-124 bp in size can be multiplexed for genotyping of individuals and provide a sensitivity of detection and a power of discrimination that would make them useful for human identification of degraded samples.

The following will describe an organization of REs and a primer design strategy that may be useful in certain embodiments of the inventive multiplex system.

In one embodiment of the present invention, synthetic primers are provided, the synthetic primers including part or full TSD sequences and being capable of amplifying specific insertion or no-insertion alleles within a multiplex system. Interpretation of the results obtained using these primers will depend upon the earlier described characterization of respective allele frequencies of dimorphic Alu repeats in various population groups. The allele frequencies of these repeats can be quite variable, ranging from as low as 0.01 for HS4.65 among US Caucasians, to as high as 0.99 for HS3.23 among African-Americans. Several of the Alu elements have heterozygosity values approaching 0.5, the theoretical maximum for bi-allelic loci. A survey of numerous dimorphic Alu repeats across several worldwide population groups reveals that approximately 80% of the markers display allele frequencies between 0.3-0.7.

For paternity testing, these frequencies are ideal for the calculation of exclusion and inclusion probabilities (Wang, J., et al., *dbRIP: A highly integrated database of retrotransposon insertion polymorphisms in humans*, Human Mutation, 27(4): 323-329 (2006)). The few markers that are present in very high frequencies within specific population groups are extremely useful for estimating the geographic origin of unknown samples in forensic casework. In general, by genotyping any unknown sample using all the dimorphic Alu repeats that have been characterized to date, it is possible to ascertain the geographic origin of the sample with a very high degree of certainty (Benson, D. A., et al., *GenBank*, Nucleic Acids Research, 33 (suppl. 1): D34-D38 (2005)).

Alus are bi-allelic with a large size difference (of ~300 base pairs) between the filled (contains Alu) and empty (absent for Alu) sites. Fundamental design flaws have appeared in Alu primer designs of the prior art. When several primer sets are multiplexed, subsequent allele "drop-out" occurs and is due to allele size differences or stochastic affects. To circumvent this issue, embodiments of the present invention provide a primer design methodology that essentially removes the intra-specific locus competition that occurs in heterozygotes (see Anderson, et al., referenced supra). This design involves utilization of the direct repeat units that flank an Alu element. The Alu and flanking direct repeat sequence make for a completely unique genomic site. There are hundreds of polymorphic Alu's that contain direct repeats (Excoffier, L., et al., *Arlequin (version 3.0): an integrated software package for population genetics data analysis*, Evolutionary Bioinformatics Online, 1: 47 (2005)). The reverse primers for filled site reactions may contain some 5' Alu sequence, the direct repeat unit and some flanking genomic sequence extending beyond the direct repeat unit. Reverse primers for empty site reactions may contain the pre-integration site and flanking genomic sequence of both sides such that the length of the oligo traverses flanking genomic sequence 5' and 3' to the pre-integration site. The 5' end of the empty site reverse primer may contain only one or two base pairs of genomic sequence beyond the pre-integration site.

FIG. 3 demonstrates the improved "mini-primer" design methodology that has been adopted in order to detect individual Alu loci. This design results in the elimination of intra-locus specific competition which reduces the potential for allele-drop out that is common in STR-based systems, especially when trace amounts of template DNA are used. Using this primer design methodology may also result in the ability to amplify nuclear DNA in a single cut/shed hair sample. Once the target site products have been amplified, they can be detected using a standard capillary electrophoresis system (ABI 310 or 3130) or micro fluidic based capillary electrophoresis systems.

The design of the primers of embodiments of the present invention, described herein and referred to subsequently as mini-primers, reduces the overall amplicon size as well as the difference in amplicon sizes between the two allelic states of INNULs. Amplification of the two alleles may occur through a common fluorescently-labeled forward primer and two unlabeled reverse primers. The labeled forward primer for the null allele may overlap the insertion site of the RE, and the unlabeled reverse primer for the insertion allele may have an overlap region with the junction and the RE itself, or just inside the RE. With this design the resulting INNUL allelic amplicons may be designed to differ by as little as one base pair. Additionally, the amplicon size can be reduced substantially, to a size much smaller than currently used STR markers, such that substantially degraded samples can be typed. With this design a more simplified and automated typing technology can be applied for LINE and SINE typing.

Selection criteria for INNUL markers to include in a multiplex depend on the application. Markers that are highly polymorphic in all major populations (i.e., approaching 50% heterozygosity) are desirable for human identity testing (LaFountain, M. J., et al., *TWGDAM Validation of the AmpFeSTR Profiler Plus and AmpFeSTR COfiler STR Multiplex Systems Using Capillary Electrophoresis*, Journal of Forensic Sciences, 46(5): 1191-1198 (2001); Moretti, T., et al., *Validation of short tandem repeats (STRs) for forensic usage: performance testing of fluorescent multiplex STR systems and analysis of authentic and simulated forensic samples*, Journal of Forensic Sciences, 46(3): 647 (2001); Budowle, B., *SNP typing strategies*. Forensic Science International, 146: S139 (2004); Syvanen, A. C., et al., referenced supra; LaRue, B. L., et al., referenced supra) while those demonstrating high coefficients of inbreeding (e.g., SNPs in which the different allelic states approach fixation in different populations) can be used for bio-ancestry analyses (see Shriver, M. D., et al., referenced supra). To demonstrate the potential of the newly designed primer sets for human identity testing that would support high quality DNA typing applications, such as in paternity testing, and low quality samples that may be encountered in criminal forensic casework, an initial set of INNUL markers based on Alu's and LINEs were chosen. The Alu based INNUL markers were selected based on molecular characteristics and extant population data (Wang, J., et al., *dbRIP: A highly integrated database of retrotransposon insertion polymorphisms in humans*, Human Mutation, 27(4): 323-329 (2006); Benson, D. A., et al., referenced supra; Cheung, K. H., et al., *ALFRED: an allele frequency database for diverse populations and DNA polymorphisms*, Nucleic Acids Research, 28(1): 361 (2000)). There was no available population data on LINE based INNUL markers, so only molecular characteristics were used as selection criteria for this study.

The ability of the patented inventive primer design to analyze heavily degraded and fragmented DNA samples is a substantial improvement over the prior art, as current forensic technologies such as mini-STR kits often give inconclusive results on such samples. In order to assess the potential of these new markers for forensic use, three fluorescently labeled markers were tested on mechanically and enzymatically degraded DNA samples. In theory, the primers designed based on the mini-primer design strategy should yield useful results on these samples even though they are degraded. Because the system relies upon the uniqueness of the repeat unit sequence in the flanking region of Alu and other Retrotransposon insertion sites, it requires only a small amplicon length, <100 bp, to give conclusive results.

For forensic casework applications, it is an absolute requirement that the primers selected can be multiplexed into a single amplification reaction. Forensic casework samples are often in very low quantity as well as being degraded. A suitable multiplexed system should be able to amplify multiple target sequences at the same time with no non-specific amplification product and also have the sensitivity to amplify DNA concentration as low as 100 pg or less. The most challenging technical task in multiplexing various markers is to co-amplify, in a single amplification, a plurality of markers with the same high sensitivity and specificity as is obtained when each marker is amplified individually. The number of markers needed within a useful system depends on the statistically calculated power of discrimination of the resulting reagent kit. Several multiplex systems containing as many as 32 markers are currently in commercial use (LaRue, B. L., et al., referenced supra). There are several published reports with guidance for achieving a successful PCR multiplex (Markoulatos, P., et al., *Multiplex Polymerase Chain Reaction: A Practical Approach*, Journal of Clinical Laboratory Analysis 16: 47-51 (2002); Schoske, R., et al., *Multiplex PCR Design Strategy Used for the Simultaneous Amplification of 10 Y Chromosome Short Tandem Repeat (STR) Loci*, Analytical & Bioanalytical Chemistry 375: 333-343 (2003); O. Henegariu, et al, *Multiplex PCR: Critical Parameters and Step-by-Step Protocol*, BioTechniques 23: 504-511 (1997); Shuber, A. P., et al., *A Simplified Procedure for Developing Multiplex PCRs*, Genome Research 5: 488-493 (1995)). The parameters to consider for developing a multiplexed PCR system are: primer length and sequence, melting temperature of each primer, relative concentration of primers, concentration of PCR buffer, balance between magnesium chloride and dNTP concentration, cycling temperatures and times, concentration of Taq DNA polymerase, and the addition of PCR modifiers. The optimization of each step for target DNA amplification is essential in order to achieve a multiplexed amplification with specificity and high sensitivity. One embodiment of the present invention, the creation of a four-dye multiplex for forensic applications, is described below.

The description herein, including the Examples below, demonstrates that by utilizing the Mini-Primer strategy, INNUL markers, which include SINEs, LINEs, and SVAs, can be effectively used as markers for human identification and bio-ancestry studies regardless of the size of the inserted element. The size of the amplicons for INNULs and the difference between allelic states can be reduced substantially such that these markers have utility for analyzing high and low quality human DNA samples. In addition, the preliminary results demonstrate that sensitivity of detection can be sufficient to enable human identity and bio-ancestry studies on forensic and anthropological samples. Depending on the markers selected and the distribution of the alleles in global populations, INNULs can be selected for human identity testing or for bio-ancestry studies.

The description herein, together with the Examples below, also demonstrates the optimization of INNUL markers into a single-tube, multi-locus reaction. The inclusion of these markers in a multiplexed reaction produces an INNUL-based human identity test set that is a powerful tool for use in many forensic settings without the need for investment in new instrumentation. The multiplexed system is able to amplify multiple target sequences at the same time with minimal non-specific amplification products and also exhibits the sensitivity to amplify DNA concentrations as low as 100 pg or less. With an amplicon size range of 46-124 base pairs, this multiplexed system contains the smallest size amplicons that are both amenable for use with extensively degraded DNA samples and generally available for use by the forensic community. Thus, the INNUL multiplex system presented in this study provides a statistically discriminating tool that is useful for forensic applications where the sample is limited in quantity as well as quality.

While this invention is particularly shown and described with reference to the embodiments described in the Examples below, those skilled in the art will recognize that other embodiments are possible without departing from the spirit and scope of the present description. For example, the PCR amplification products of the methods and systems described herein may be characterized using Next Generation Sequence analysis (NGS) analysis methods (Mak, H. C., *Next-Generation Sequence Analysis*, Nature Biotechnology 29: 45-46 (2011); Metzker, M. L., *Sequencing Technologies—The Next Generation*, Nature Reviews/Genetics 11: 31-46 (2010)). Additional embodiments of the invention may make use of rapid DNA analysis platforms (see, e.g., Khandurina, et al., Integrated System for Rapid PCR-Based DNA Analysis in Microfluidic Devices, Analytical Chemistry 72: 2995-3000 (2000)) for characterization of the PCR amplification products of the methods and systems of the invention. In other embodiments, practitioners may find that labeling the reverse primers instead of labeling the forward primers is more effective for a particular purpose.

EXAMPLES

Example 1

A Four Dye Multiplex System for Forensic Applications

A number of markers were selected for multiplexing for a forensically useful kit. The forward primers for each marker were labeled with one of three fluorophores, 6-carboxyfluorescein (sold as 6-FAM), 6-carboxy-4',5'-dichloro-2',7'-dimethoxyfluorescein (sold as JOE), or 6-carboxytetramethylrhodamine (sold as TAMRA) (using 6-carboxy-X-rhodamine (sold as ROX) and a fifth fluorophore in the orange wavelength range as the size standard). The selected markers' amplicons range in size between approximately 46 and 124 bp, and individual. INNUL alleles differ in amplicon size between 3 and 8 bps. The gender marker Amelogenin was also added to the multiplex. Multiplex optimization experiments addressing primer concentration and peak heights were performed.

Markers were selected from dbRIP, a database of retrotransposon insertion polymorphisms in humans presented on the interact under the auspices of Brock University, from existing literature, and through BLAST sequence analysis (A. F. A. Smit, et al.; Batzer, M. A., et al. (2002); Batzer, M. A., et al. (1994); Feng, Q., et al.; Houck, C. M., et al.; Kazazian, H. H., et al.; Ostertag, E. M., et al.; Ustyugova, S. V., et al.; Mamedov, I. Z., et al.; Novick, G. E., et al.; Wang, J., et al. (2006), all referenced supra; McGinnis, S., et al., *BLAST: at the core of a powerful and diverse set of sequence analysis tools*, Nucleic Acids Research 32(suppl 2): W20-W25 (2004)). After initial selection, the potential loci were assessed for their suitability for primer design (Zangenberg, G., et al., referenced supra).

Genomic DNA was extracted from human buccal swabs using ChargeSwitch® gDNA Buccal Cell Kit (Invitrogen) via magnetic bead separation. All extractions were run with a reagent blank. Samples were stored at −20° C. until amplification.

Extracted samples were quantified using the Quantifiler® Human DNA Quantification Kit (Applied Biosystems) or the InnoQuant™ Human DNA Quantification & Degradation Assessment Kit offered by innoGenomics and performed on the 7500 Real-Time PCR System (Applied Biosystems). The cycle conditions were based upon the Quantifiler™ Kit or InnoQuant™ Kit User's Manual (Applied Biosystems, 2010). The data was analyzed using the HID Real-Time PCR Analysis Software v1.1 (Applied Biosystems) with a threshold value set per the manufacturer recommendations.

Example 2

Primer Design

Primers were designed using Primer3 (input version 0.4.0. http://frodo.wi.mit.edu/primer3/). A set of three primers was designed for each marker: one forward primer and two reverse primers, one for the insertion and one for the null allele. All of the designed primers have $T_m$ values in the range of 58°-61° C. The program "Reverse Complement" from the Harvard Medical Technology Group and Lipper Center for Computational Genomics was used (arep.med.harvard.edu/). Subsequently, the primers were screened against the GenBank non-redundant database (National Center for Biotechnology Information, U.S. National Library of Medicine, National Institutes of Health) to determine whether they were unique DNA sequences. Table 1 provides the available markers, and Table 2 provides the primer sequences used for the selected markers.

TABLE 1

RE markers available for selection.

| | Selected Marker | Chromosome | Type | Reverse Empty (bp) | Reverse Filled (bp) | Location | Band | Gene ID |
|---|---|---|---|---|---|---|---|---|
| 1 | CH1-6217 | 1 | LINE | 160 | 157 | chr1: 219894446-219894446 | 1q41 | chr1-2182; 1104685475315; RIP_L1_chr1_218_01 |
| 2 | pAlu1-2767 | 1 | Alu | 101 | 101 | chr1: 26362411-26362722 | 1p36.11 | pAlu1-25722767; RIP_Alu_chr1_026_01 |
| 3 | TARBP1R | 1 | Alu | 65 | 60 | chr1: 234,527,060-234,614,849 | 1q42.2 | AL136124.10; 33110_33420Sdel |
| 4 | Ya5-MLS48 | 2 | Alu | 87 | 81 | chr 2: 74,024,900-74,034,900 | 2p13.1 | AC073577.32; 48284_48612del |
| 5 | LC3-2601 | 3 | LINE | 178 | 127 | chr3: 26414512-26420540 | 3p24.1 | 238595; L1HS364; RIP_L1_chr3_026_01 |
| 6 | Yb8AC1141 | 3 | Alu | 66 | 61 | chr3: 96598900-96599212 | 3q11.2 | pAlu3-96397335; RIP_Alu_chr3_096_01 |
| 7 | Ya5NBC51 | 3 | Alu | 122 | 122 | chr3: 191773344-191773631 | 3q28 | Ya5NBC345; RIP_Alu_chr3_191_01 |
| 8 | HS4.69R | 5 | Alu | 114 | 107 | chr5: 164366293-164366709 | 5q14.3 | NT_023133 |
| 9 | CH26240 | 5 | LINE | 153 | 132 | chr5: 151436625-151442640 | 5q33.1 | L1HS446; Druze75; RIP_L1_chr5_151_01 |
| 10 | Ya5NBC327 | 6 | Alu | 131 | 127 | chr6: 50560439-50560754 | 6p12.3 | RIP_Alu_chr6_050_01 |
| 11 | CH6-28-9163 | 6 | LINE | 112 | 115 | chr6: 19873106-19879163 | 6p22.3 | AL022726; RIP_L1_chr6_019_01; AC206603 |
| 12 | Ya5ACA1736 | 8 | Alu | 112 | 109 | chr8: 126093295-126093295 | 8q24.13 | pAlu8-125692903; RIP_Alu_chr8_126_01 |

TABLE 1-continued

RE markers available for selection.

| | Selected Marker | Chromosome | Type | Reverse Empty (bp) | Reverse Filled (bp) | Location | Band | Gene ID |
|---|---|---|---|---|---|---|---|---|
| 13 | Ya5NBC239 | 9 | Alu | 69 | 65 | chr9: 118516900-118517218 | 9q33.1 | RIP_Alu_chr9_116_01 |
| 14 | Yb7AD155 | 10 | Alu | 102 | 101 | chr10: 10493725-10493824 | 10q21.1 | gi\|224514932\|ref\|NT_008705.16 |
| 15 | Ya5-MLS18 | 11 | Alu | 79 | 76 | chr11: 24749534-24749534 | 11p14.3 | RIP_Alu_chr11_024_01 |
| 16 | CH4-12-7012 | 12 | LINE | 150 | 122 | chr4: 20769969-20775752 | 4p15.31 | L1HS39; RIP_L1_chr4_016_01 |
| 17 | Y5ac2305 | 13 | Alu | 67 | 68 | chr13: 38926483-38926791 | 13q13.3 | RIP_Alu_chr13_038_01 |
| 18 | Yac52265 | 13 | Alu | 108 | 103 | chr13: 102807866-102808174 | 13q33.1 | pAlu13-102846400; 79718; RIP_Alu_chr13_102_01 |
| 19 | CH14-50-6236 | 14 | LINE | 175 | 127 | chr14: 82705608-82706236 | 14q31.2 | 238908; L1AD253; RIP_L1_chr14_082_01 |
| 20 | Ya5NBC241 | 15 | Alu | 104 | 103 | chr15: 41447735-41448045 | 15q15.3 | 238740; RIP_Alu_chr15_041_01 |
| 21 | Yb8NBC13 | 17 | Alu | 99 | 92 | chr16: 26515540-26515866 | 16p12.1 | pAlu16-26535378; RIP_Alu_chr16_026_02 |
| 22 | Yb8AC1796 | 18 | Alu | 100 | 100 | chr18: 42592433-42592753 | 18q21.1 | RIP_Alu_chr18_042_01 |
| 23 | CHR20-79712 | 20 | LINE | 104 | 102 | chr20: 11465280-11465588 | 20p12.2 | 79712; RIP_Alu_chr20_011_01 |
| 24 | YbSNBC106 | 21 | Alu | 129 | 123 | chr21: 40508751-40509060 | 21q22.2 | RIP_Alu_chr21_040_01 |
| 25 | Ch22-Ya5533 | 22 | LINE | 112 | 115 | chr22: 14733466-14733466 | 22q11.1 | Ya5533; RIP_Alu_chr22_014_01 |
| 26 | MLS9 | 1 | Alu | 120 | 115 | — | 1q25.3 | AK023131.1, 1453_1773del |
| 27 | YA5-MLS26 | 3 | Alu | 84 | 81 | — | 3p22.1 | AY736289; 157_483del |
| 28 | AC4027 | 7 | Alu | 70 | 64 | — | 7q21.11 | AC004027.1; 997_1332del |
| 29 | SVA306 | 14 | SVA | 71 | 74 | chr14: 64430151-64433293 | 14q23.3 | SPTB; H14_E_66; RIP_SVA_chr14_064_01; dbRIP ID: 3000006 |
| 30 | SVA323 | 3 | SVA | 120 | 117 | chr3: 195602463-195603210 | 3q29 | AFURS1; RIP_SVA_chr3_195_01; dbRIP ID: 3000023 |

TABLE 2

Primer sequences used for each INNUL marker and the resulting amplicon size produced.

| Marker | Forward Sequence | Reverse Empty Sequence | Reverse Filled Sequence | Amplicon Size of Empty Allele | Amplicon Size of Filled Allele |
|---|---|---|---|---|---|
| CHR20-79712 | [6-FAM]ATTTGCACAGTGCTCCACAC SEQ ID NO: 61 | GTTGCACGTAAGACAGAATTTGA SEQ ID NO: 2 | GCGGCCAAGACAGAATTGA SEQ ID NO: 3 | 55 | 53 |
| Ya5-MLS48 | [6-FAM]TTGGCTTGTAAACTAATTGCTG SEQ ID NO: 62 | GCAAAGCAACTTGCACCTTTTCTA SEQ ID NO: 5 | GCGGCCGCACCTTTTCTATTG SEQ ID NO: 6 | 81 | 74 |
| Yb8NBC13 | [6-FAM]TCTGGCAAATGCTACCCAAGT SEQ ID NO: 63 | GCTGAAGCATCTTCCTCTTCACA SEQ ID NO: 8 | GCGGCCCCTCTTCACATCTTA SEQ ID NO: 9 | 96 | 91 |
| Ya5ACA1736 | [6-FAM]CCTGCTCTGCACACTTCTTG SEQ ID NO: 64 | GACCTTGACCTAGAGAAGGCAAT SEQ ID NO: 11 | GCCGAGAAGGCAATTTTCTA SEQ ID NO: 12 | 109 | 100 |
| Yb8NBC106 | [6-FAM]CATCAAACTCCAGAGTTCCTAAG SEQ ID NO: 65 | GATTGATGAGGACTCAGGTTGA SEQ ID NO: 14 | GGATTACAGGCGTGAGGATT SEQ ID NO: 15 | 121 | 117 |
| Y5ac2305 | [JOE]TGGTGACACTCCAATTTCTTCT SEQ ID NO: 66 | GGCATCCTTTGATTACAACTCTTA SEQ ID NO: 17 | GCCCCAATTACAACTCTTAAGGAAA SEQ ID NO: 18 | 52 | 49 |

TABLE 2-continued

Primer sequences used for each INNUL marker and the resulting amplicon size produced.

| Marker | Forward Sequence | Reverse Empty Sequence | Reverse Filled Sequence | Amplicon Size of Empty Allele | Amplicon Size of Filled Allele |
|---|---|---|---|---|---|
| HS4.69 | [ROX]TGCCAGGTGATAGT ATTAGGAGGTG SEQ ID NO: 67 | GGCATCGTATCTATTCAT GTGATTTTTA SEQ ID NO: 20 | CCGGCCTATTCATGTGA TTT SEQ ID NO: 21 | 81 | 77 |
| AC4027 | [JOE]AAGGTCTAAGCGCA GTGGAA SEQ ID NO: 68 | GTGTTTTGTACAGAGTTC TTAATTGC SEQ ID NO: 23 | GGCCCAGAGTTCTTAAT TGC SEQ ID NO: 24 | 70 | 64 |
| CH1-6217 | [JOE]TGGCCCACCTATGTC TAAAA SEQ ID NO: 69 | GTTGATTCAAAGCAACC AATCC SEQ ID NO: 26 | GTCAAGGCAAACCAAT CCAA SEQ ID NO: 27 | 81 | 77 |
| Yb8AC1796 | [JOE]TGCCAGACAGCAAA CAAATA SEQ ID NO: 70 | GCAAGGTCACAGGTAGG CTTTTTA SEQ ID NO: 29 | GGCCACAGGTAGGCTT TTTA SEQ ID NO: 30 | 95 | 90 |
| Yac52265 | [JOE]AGAAGAGTGAATGC ACATTTATGA SEQ ID NO: 71 | GGAGTCATGAATTCAGT TTCTTA SEQ ID NO: 32 | GCCCGGCCCAGTTTCTT A SEQ ID NO: 33 | 104 | 100 |
| MLS9 | [JOE]AGCAGATTTCAGGTC ATTATTGTTT SEQ ID NO: 72 | GTTTCTCTCAGAAGCTAT CTCAATTTTAA SEQ ID NO: 35 | GCGGCCTGCTATCTCAA TTT SEQ ID NO: 36 | 120 | 115 |
| TARBP1 | [TMR]AAGGAGGCAAAGG AAGAATACA SEQ ID NO: 73 | GTTGATCCAGTCATTCAT CATTTTAT SEQ ID NO: 38 | GCGGCCCATTCATCAGT TT SEQ ID NO: 39 | 65 | 60 |
| SVA306 | [TAMRA]TGGAGGCCTCTG CTATTTTC SEQ ID NO: 74 | GAAGGGTTCATTAAAGA ATTTTCATAG SEQ ID NO: 41 | GAGAGGGAGAGGGACA AGAA SEQ ID NO: 42 | 71 | 74 |
| Amelogenin | [TMR]CCCTTTGAAGTGGT ACCAGAGCA SEQ ID NO: 75 | GCATGCCTAATATTTTCA GGGAATA SEQ ID NO: 44 | * | X = 81 | Y = 84 |
| SVA323 | [TMR]TGTGCTTCATTTGAG AAAGCTG SEQ ID NO: 76 | GCTGGCCGGAAGTCTTA ATGC SEQ ID NO: 47 | GTTGAAGGATAGAAGT CTTAATGCAG SEQ ID NO: 48 | 120 | 117 |
| Ya5NBC51 | [ROX]TCGCCATCTCTTCTT CCTTCA SEQ ID NO: 77 | GTCCAGGGTTAATGCTTT GT SEQ ID NO: 50 | GACAGGCGTGAGAATG CTTTG SEQ ID NO: 51 | 122 | 124 |
| Yb8AC1141 | [ROX]ACAAATACTACAGA CAAAAGCTACTGA SEQ ID NO: 78 | GAACCCCACCAACCTGA CT SEQ ID NO: 53 | GGCCCAACCTGACTTA CT SEQ ID NO: 54 | 66 | 59 |
| Yb7AD155 | [ROX]TGTACACATTAAGC ACATGGAAGTCA SEQ ID NO: 79 | GCATGAAATGTTCTTTTT CATCT SEQ ID NO: 56 | GCCCGGCCGTTCTTTTT C SEQ ID NO: 57 | 102 | 101 |
| Ya5-MLS18 | [ROX]AACTTCAAGGTATT TGCATCATG SEQ ID NO: 80 | TGCTAGCTAACTCTCTAA GGTCTT SEQ ID NO: 59 | CCGGCCTCTAAGGTCTT TTT SEQ ID NO: 60 | 117 | 111 |

Example 3

Primer Preparation

The fluorescently labeled and unlabeled oligonucleotide primers were synthesized by Eurofins MWG Operon (Huntsville, Ala., USA) or Integrated DNA Technologies (Skokie, Ill.). All lyophilized primers (labeled and unlabeled) were dissolved in 10 mM TE (tris(hydroxymethyl) aminomethane ("Tris") and ethylenediamine tetraacetic acid ("EDTA")) Buffer (pH 8.0) to a 100 µM stock concentration (10×). The stock primers were stored at 4° C. until used. Following reconstitution, each primer was diluted using TE Buffer to a final concentration of 10 µM (1×). Each primer mix consisted of three primers: one labeled forward primer and two corresponding unlabeled reverse primers. The combined volume of the two reverse primers was equivalent to the volume of the forward primer. All labeled primers were stored in opaque polypropylene tubes to avoid quenching of the fluorescent tags.

Example 4

Amplification of Labeled Primers

All labeled markers were amplified using the GeneAmp® PCR System 9700 thermal cycler (Applied Biosystems). The final concentrations of reaction components (Bio-Rad) were as follows: 1.25U iTaq DNA Polymerase, 10× iTaq buffer, 5 mM MgCl$_2$ and 100 µM dNTP mix. The volumes of each component are as follows: 0.125 µL of iTaq DNA Polymerase, 2.5 µL of iTaq buffer, 2.5 µL of MgCl$_2$, 0.5 µL of dNTP mix, 17.375 µL of nuclease-free water, 1 µL of primer mix and 1 µL of 0.5 ng DNA, bringing the final reaction volume to 25 µL. All runs included 0.5 ng/µL of K562 DNA standard (Promega Corporation) as a positive control and negative control. All labeled markers were amplified using the same conditions:
Cycling parameters:

| | | |
|---|---|---|
| 95° C. for 3 min | 95° C. for 0.30 min \| <br> 60° C. for 0.30 min \| <br> 32 cycles <br> 72° C. for 0.30 min \| | 72° C. for 10.00 min <br> 4° C. for Infinite Time |

Example 5

Data Analysis Using ABI 310 and 3130 Capillary Electrophoresis Systems

After amplification, samples were prepared by combining 20 µL of Hi-Di™ formamide, 0.25 µL of 350 ROX™ (or CC5 Internal Lane Standard 500) size standard and 1 µL of DNA product per reaction. Samples were incubated at 95° C. for 3 minutes. Separation and detection of STR amplification products were performed on an ABI Prism® 310 Genetic Analyzer (Applied Biosystems) using the following parameters for the GS STR POP4 (1 ml) F module: injection at 15 kV for 5 seconds, 15 kV separation at 60° C., run time of 28 minutes. Separation and detection of STR amplification products were performed on an ABI Prism® 3130 Genetic Analyzer (Applied Biosystems) using the following parameters for the GS STR POP4 (1 ml) G5v2 module: injection at 1.2 kV for 12 seconds, data delay time at 1 second and run time at 960 seconds. Data was analyzed using the GeneMapper ID Software version 3.2 (Applied Biosystems).

Electropherograms were interpreted based on peak height and allele drop-out for each marker when compared to the control, based on a minimum detection threshold of 50 RFUs. A macro was created for each marker to identify all peaks as either Insertion or No Insertion and to determine the peak height and amplicon size. The labeled markers were then tested for quality control and reproducibility, re-amplifying DNA samples with all three genotypes (heterozygote, No Insertion homozygote, and Insertion homozygote) to ensure that accurate profiles were obtained.

Example 6

Design of a Multiplex for Simultaneous Amplification of Fifteen Markers

Fifteen RE markers and Amelogenin were multiplexed to provide simultaneous amplification of all the Insertion and No-Insertion alleles for each marker in a four-dye system. The expected sizes of markers are presented in FIG. 4. For each of the fifteen markers and Amelogenin, Table 3 shows the dye attached to the associated forward primer, the type of allele, the sequence lengths of corresponding null and insertion alleles and the chromosome number corresponding to the location in the genome where the allele is found.

TABLE 3

Multiplex markers showing Name, Type, Dye label, Chromosomal location and Amplicon

| | Selected Marker | Dye | Type | Null Allele Size (bp) | Insertion Allele Size (bp) | Chromosome Number |
|---|---|---|---|---|---|---|
| 1 | CHR20-79712 | FAM | LINE | 56 | 52 | 20 |
| 2 | Ya5-MLS48 | FAM | Alu | 79 | 73 | 2 |
| 3 | Ya5ACA1736 | FAM | Alu | 108 | 99 | 8 |
| 4 | Yb8NBC106 | FAM | Alu | 119 | 115 | 21 |
| 5 | Yb8AC1141 | JOE | Alu | 58 | 52 | 3 |
| 6 | Ya5-MLS18 | JOE | Alu | 73 | 70 | 11 |
| 7 | Yb8NBC13 | JOE | Alu | 87 | 90 | 16 |
| 8 | Yac52265 | JOE | Alu | 101 | 97 | 13 |
| 9 | MLS9R | JOE | Alu | 118 | 112 | 1 |
| 10 | TARBP1R | TMR | Alu | 59 | 55 | 1 |
| 11 | Amelogenin | TMR | — | X = 79 | Y = 82 | X & Y |
| 12 | Ya5NBC241 | TMR | Alu | 98 | 93 | 15 |
| 13 | HS4.69R | TMR | Alu | 114 | 109 | 5 |
| 14 | YaSNBC51 | TMR | Alu | 120 | 124 | 3 |
| 15 | Ya5ACA1766 | ROX | Alu | 68 | 63 | 8 |
| 16 | CH1-2250 | ROX | LINE | 105 | 102 | 1 |

The markers were selected, and the system was optimized as follows:

Initial efforts towards marker selection focused on the set of forensic candidate markers discussed in Mamedov, et al., referenced supra. Using these markers as a benchmark, and the previously described Mini-Primer strategy, an attempt was made to reduce the amplicon size of a subset of markers from Mamedov, et al., referenced supra. Primers for five markers were designed such that all amplicons were less than 120 bp in size for both the insertion and null alleles. Gel electrophoresis was used to visualize the products of the reactions. This result supported the validity of the Mini-Primer strategy.

Following this initial success, RE markers (Alu's, LINES and SVA) were chosen from the literature (Batzer, M. A., et al. (1994); Feng, Q., et al.; Ustyugova, S. V., et al.; Mamedov, I. Z., et al.; Novick, G. E., et al.; Wang, J., et al.; McGinnis, S., et al., all referenced supra). Through analysis of amplicon size and analytical performance of individual markers, a set of candidate markers were selected to demonstrate the validity of the Mini-Primer approach for multiplexing INNULs. These loci are described in Table 1. Once selected, the primer concentration for each marker was optimized. Heterozygous samples for each marker were balanced and the peak height ratios were determined. Optimization through increasing the primer concentration of "weak" alleles and decreasing the primer concentration of "strong" alleles was performed in a series of reactions. Using the same DNA samples, the peaks for each marker were rebalanced in a multiplex by adding the markers to reactions in a stepwise fashion. Most markers already exhibited balanced peaks while other primer mix ratios were modified.

The selected markers for multiplexing represent a total of 20 markers, 15 Alu's, and 2 LINEs, 2 SVAs and Amelogenin with amplicons that are between 46 and 124 bp in length. FIG. 5 shows an example electropherogram of the size range of alleles for 9 multiplexed RE markers and Amelogenin. Thus, it is feasible to generate amplified products of the allelic states of Alu's, LINEs and SVAs in a multiplexed reaction that is more suited for forensic samples and in actuality is better suited for high quality samples as well. When the size is similar for amplified products of allelic states, assays tend to be more robust and demonstrate less preferential amplification of the smaller sized allele.

Example 7

Optimization of the Multiplex Reaction for Simultaneous Amplification of Fifteen Markers Primer quality was assured as follows. One of the biggest hurdles to optimizing the multiplex reaction for primers that produce products with large PCR product size differences is allele drop out of larger alleles due to preferential amplification of the shorter product. This issue is addressed by designing the primers with comparable allele sizes (generally between 2-8 bp difference between the Empty and Filled alleles). Primer designs were performed using Primer 3 software. For each primer the $T_m$ value calculated using a default salt concentration was within 5° C. (57°-62° C.). Primer nucleotide composition and sequences were examined to eliminate primer-primer interaction in order to prevent the primers from binding among themselves rather than the target DNA template.

Primer modification with "G" tail and fluorescent dye labeling is another way to improve the quality of the data. During amplification, Taq DNA polymerase often adds an extra Adenosine (A) nucleotide at the 3' end of the product (Magnuson V. L., et. al., *Substrate Nucleotide-Determined Non-Templated Addition of Adenine by Taq DNA Polymerase: Implications for PCR-Based Genotyping and Cloning*, BioTechniques 21(4): 700-709 (1996)). The resulting product is termed "+A" product. The extent of this extra A addition depends on the sequence at the 5' end of the opposing primer. This gives a split peak with "−A" and +A, one base difference in size of the PCR product. Brownstein and coworkers (Brownstein M. J., et. al., *Modulation of Non-Templated Nucleotide Addition by Taq DNA Polymerase: Primer Modifications that Facilitate Genotyping*, BioTechniques 20(6): 1004-1006, 1008-1010 (1996)) reported that if the nucleotide on the 5' terminus of the unlabeled primer is a Guanine (G), complete addition of A is favored and the resulting product is homogeneous. The presence of a G adjacent to the dye label decreases the fluorescence intensity and thus the detection of +A/−A products is avoided. To avoid +A/−A products with many of the primer sets, an extra step at the end of the amplification cycle, for 10 minutes at 72° C. is performed.

An optimum concentration of the primers for use in the multiplex reaction was found as follows. Initially, five markers labeled with 6-carboxyfluorescein (sold as 6-FAM) were multiplexed using 1.0 μL, 1.5 μL and 2.0 μL of each primer mix per reaction. Samples were then amplified and analyzed using the Amplification of Labeled Primers and Data Analysis for ABI 310 or 3130 protocols, respectively. Results suggest that 1 μL of primer mix was more effective and showed optimum peak heights of 1000-2000 RFUs when compared to 1000 RFUs and 500 RFUs for 1.5 μL and 2 μL respectively. 1 μL of each primer mix was used when performing the peak ratio test for multiplexed samples. Heterozygous samples were used to assess peak balance and optimize peak height ratios.

The $MgCl_2$ concentration used in the multiplex reaction was optimized. Optimization of the $Mg^{2+}$ ion was performed for each selected marker individually. Final concentrations of $MgCl_2$ tested were 1.5 mM, 2.0 mM, and 2.5 mM. A 2.5 mM concentration was selected due to optimal peak morphology and balance, and reduction of non-specific artifacts at this concentration.

Example 8

Population and Statistical Analyses

Two North American sample populations (African American, N=134; and Caucasian, N=48; were typed for the 15 INNUL loci. The frequencies of the No-Insertion (N) allele and Insertion (I) allele per locus were determined. Observed heterozygosity, random match probability, and power of discrimination were calculated. Heterozygosities for the markers' departures from linkage equilibrium (i.e., linkage disequilibrium (LD) between pairs of loci) were tested for each of the two populations. Markers with allele frequencies that differ substantially in one or more of the populations tend to be more useful for bio-ancestry studies. Parentage analysis of 100 cases containing samples from mother, child, and alleged father from Caucasian and African American populations were analyzed using the 16 marker (15 RE's and Amelogenin) multiplex referred as InnoTyper™. Results for father and mother samples from African American and Caucasian populations were used for allele frequencies and genotype frequencies and are presented in Table 4 and Table 5.

TABLE 4

Population studies data: Allele frequencies for Caucasian and African American DNA samples obtained by analyzing using 15 RE's Marker Multiplex (InnoTyper ™).
Table 5: Allele Frequencies for 15 Markers

| MARKER | ALLELE | IN BLACKS | | IN CAUCASIAN | |
|---|---|---|---|---|---|
| | | NUMBER | PER-CENT | NUMBER | PER-CENT |
| 79712 | I | 0.347 | 34.7 | 0.4896 | 48.96 |
| | N | 0.653 | 65.3 | 0.5104 | 51.04 |
| MLS48 | I | 0.3694 | 36.94 | 0.7813 | 78.13 |
| | N | 0.6306 | 63.06 | 0.2188 | 21.88 |
| 1736 | I | 0.3769 | 37.69 | 0.2083 | 20.83 |
| | N | 0.6231 | 62.31 | 0.7917 | 7917 |
| NBC106 | I | 0.5336 | 53.36 | 0.4167 | 41.67 |
| | N | 0.4664 | 46.64 | 0.5834 | 58.34 |
| 1141 | I | 0.2574 | 25.74 | 0.5625 | 56.25 |
| | N | 0.7425 | 74.25 | 0.4375 | 43.75 |
| MLS18 | I | 0.5714 | 57.14 | 0.6875 | 68.75 |
| | N | 0.4286 | 42.86 | 0.3125 | 31.25 |
| NBC13 | I | 0.6567 | 65.67 | 0.3646 | 36.46 |
| | N | 0.3439 | 34.39 | 0.6354 | 63.54 |
| 2265 | I | 0.3993 | 39.93 | 0.7083 | 70.83 |
| | N | 0.6007 | 60.07 | 0.2917 | 29.17 |
| MLS9 | I | 0.2201 | 22.01 | 0.4583 | 45.83 |
| | N | 0.7799 | 77.99 | 0.5417 | 54.17 |
| TARBP1 | I | 0.2836 | 28.36 | 0.5938 | 59.38 |
| | N | 0.7164 | 71.64 | 0.4062 | 40.62 |
| NBC241 | I | 0.1269 | 12.69 | 0.6979 | 69.79 |
| | N | 0.8731 | 87.31 | 0.3021 | 30.21 |
| HS4.69R | I | 0.3022 | 30.22 | 0.3958 | 39.58 |
| | N | 0.6978 | 69.78 | 0.6042 | 60.42 |
| NBC51 | I | 0.4328 | 43.28 | 0.25 | 25 |
| | N | 0.5671 | 56.71 | 0.75 | 75 |
| 1766 | I | 0.7351 | 73.51 | 0.6562 | 65.62 |
| | N | 0.2649 | 26.49 | 0.3438 | 34.38 |
| 2250 | I | 0.0821 | 8.21 | 0.25 | 25 |
| | N | 0.9179 | 91.79 | 0.75 | 75 |

TABLE 5

Population studies: Genotype frequencies of Caucasian and African American populations for 15 RE markers analyzed using the multiplex system.
Table 6: Genotype Frequencies for 15 Markers

| MARKER | GENOTYPE | IN BLACK NUMBER | IN BLACK PERCENT | IN CAUCASIAN NUMBER | IN CAUCASIAN PERCENT |
|---|---|---|---|---|---|
| 79712 | I, I | 18 | 13.43 | 10 | 20.83 |
|  | I, N | 57 | 42.54 | 27 | 56.25 |
|  | N, N | 59 | 44.03 | 11 | 22.92 |
| MLS48 | I, I | 21 | 15.67 | 29 | 60.42 |
|  | I, N | 57 | 42.54 | 17 | 35.42 |
|  | N, N | 56 | 41.79 | 2 | 4.17 |
| 1736 | I, I | 16 | 11.94 | 3 | 6.25 |
|  | I, N | 69 | 51.49 | 14 | 29.17 |
|  | N, N | 49 | 36.57 | 31 | 64.58 |
| NBC106 | I, I | 44 | 32.84 | 7 | 14.58 |
|  | I, N | 55 | 41.04 | 26 | 54.17 |
|  | N, N | 35 | 26.12 | 15 | 31.25 |
| 1141 | I, I | 7 | 5.22 | 17 | 35.42 |
|  | I, N | 55 | 41.04 | 20 | 41.67 |
|  | N, N | 72 | 53.73 | 11 | 22.92 |
| MLS18 | I, I | 61 | 45.86 | 25 | 52.08 |
|  | I, N | 30 | 22.56 | 16 | 33.33 |
|  | N, N | 42 | 31.58 | 7 | 14.58 |
| NBC13 | I, I | 86 | 64.18 | 14 | 29.17 |
|  | I, N | 4 | 2.99 | 7 | 14.58 |
|  | N, N | 44 | 32.84 | 27 | 56.25 |
| 2265 | I, I | 22 | 16.42 | 28 | 58.33 |
|  | I, N | 63 | 47.01 | 12 | 25 |
|  | N, N | 49 | 36.57 | 8 | 16.67 |
| MLS9 | I, I | 4 | 2.99 | 10 | 20.83 |
|  | I, N | 51 | 38.06 | 24 | 50 |
|  | N, N | 79 | 58.96 | 14 | 29.17 |
| TARBP1 | I, I | 11 | 8.21 | 18 | 37.5 |
|  | I, N | 54 | 40.3 | 21 | 43.75 |
|  | N, N | 69 | 51.49 | 9 | 18.75 |
| AMEL | XX | 63 | 47.01 | 23 | 47.92 |
|  | XY | 71 | 52.99 | 25 | 52.08 |
| NBC241 | I, I | 1 | 0.75 | 24 | 50 |
|  | I, N | 32 | 23.88 | 19 | 39.58 |
|  | N, N | 101 | 75.37 | 5 | 10.42 |
| HS4.69R | I, I | 11 | 8.21 | 7 | 14.58 |
|  | I, N | 59 | 44.03 | 24 | 50 |
|  | N, N | 64 | 47.76 | 17 | 35.42 |
| NBC51 | I, I | 46 | 34.33 | 9 | 18.75 |
|  | I, N | 24 | 17.91 | 6 | 12.5 |
|  | N, N | 64 | 47.76 | 33 | 68.75 |
| 1766 | I, I | 72 | 53.73 | 22 | 45.83 |
|  | I, N | 53 | 39.55 | 19 | 39.58 |
|  | N, N | 9 | 6.72 | 7 | 14.58 |
| 2250 | I, I | 0 | 0 | 4 | 8.33 |
|  | I, N | 22 | 16.42 | 16 | 33.33 |
|  | N, N | 112 | 83.58 | 28 | 58.33 |

Parentage analysis of 100 cases containing samples from mother, child, and alleged father were analyzed for the following parameters:

RMP=Random Match Probability (sum of squares of three genotype frequencies under HWE assumption)
PD=Probability of Discrimination=1−RMP
PE (Trio)=Paternity Exclusion Probability with data on Trio (i.e., mother-child-Alleged father)=H(2−H)/4, where H is the expected Heterozygosity for a bi-allelic locus under HWE
PE (Def)=Paternity Exclusion Probability in motherless cases (i.e., with data on child and Alleged father only)=½·H²
PI(min)=Minimum Paternity Index (for a non-excluded allege father)=1/{4(1−p)}, where p is the frequency of the rarer allele of a bi-allelic locus
PI(max)=Maximum Paternity Index (for a non-excluded allege father)=1/p, where p is the frequency of the rarer allele of a bi-allelic locus The results are summarized in Table 6 and Table 7.

TABLE 6

Estimates of Forensic and Parentage Testing Parameters of the 15 Markers in the Caucasian Population

| Marker | RMP | PD | PE (Trio) | PE (Def) | PI (min) | PI (Max) |
|---|---|---|---|---|---|---|
| 79712 | 0.3751 | 0.6249 | 0.1875 | 0.1249 | 0.4898 | 2.0425 |
| MLS48 | 0.4917 | 0.5083 | 0.1417 | 0.0584 | 0.3200 | 4.5725 |
| 1736 | 0.3915 | 0.6085 | 0.1797 | 0.1103 | 0.4012 | 2.6532 |
| NBC106 | 0.3761 | 0.6239 | 0.1869 | 0.1239 | 0.4685 | 2.1441 |
| 1141 | 0.4545 | 0.5454 | 0.1546 | 0.0731 | 0.3367 | 3.8835 |
| MLS9 | 0.4902 | 0.5098 | 0.1422 | 0.0589 | 0.3206 | 4.5434 |
| TARBP1 | 0.4350 | 0.5650 | 0.1619 | 0.0825 | 0.3490 | 3.5261 |
| NBC241 | 0.6305 | 0.3695 | 0.0985 | 0.0246 | 0.2863 | 7.8802 |
| HS4.69R | 0.4233 | 0.5767 | 0.1663 | 0.0889 | 0.3583 | 3.3091 |
| 1766 | 0.4196 | 0.5804 | 0.1679 | 0.0911 | 0.3401 | 3.7750 |
| 2250 | 0.7327 | 0.2673 | 0.0697 | 0.0114 | 0.2724 | 12.1803 |
| MLS18 | 0.3803 | 0.6197 | 0.1849 | 0.1200 | 0.4375 | 2.3332 |
| NBC13 | 0.4032 | 0.5968 | 0.1746 | 0.1017 | 0.3807 | 2.9129 |
| NBC51 | 0.3796 | 0.6204 | 0.1852 | 0.1205 | 0.4408 | 2.3105 |
| 2265 | 0.3858 | 0.6142 | 0.1823 | 0.1151 | 0.4162 | 2.5044 |
| Combined 15 loci | $4.85 \times 10^{-6}$ | 0.999995 | 0.9263 | 0.7474 | $3.22 \times 10^{-7}$ | 156 million |

TABLE 7

Estimates of Forensic and Parentage Testing Parameters of the 15 Markers in the African-American Population

| Marker | RMP | PD | PE (Trio) | PE (Def) | PI (min) | PI (Max) |
|---|---|---|---|---|---|---|
| 79712 | 0.4017 | 0.5983 | 0.1753 | 0.1027 | 0.3828 | 2.8818 |
| MLS48 | 0.3938 | 0.6062 | 0.1787 | 0.1085 | 0.3964 | 2.7071 |
| 1736 | 0.3915 | 0.6085 | 0.1797 | 0.1103 | 0.4012 | 2.6532 |
| NBC106 | 0.3761 | 0.6239 | 0.1869 | 0.1239 | 0.4685 | 2.1441 |
| 1141 | 0.4545 | 0.5455 | 0.1546 | 0.0731 | 0.3367 | 3.8835 |
| MLS9 | 0.4902 | 0.5098 | 0.1422 | 0.0589 | 0.3206 | 4.5434 |
| TARBP1 | 0.4350 | 0.5650 | 0.1619 | 0.0825 | 0.3490 | 3.5261 |
| NBC241 | 0.6305 | 0.3695 | 0.0985 | 0.0246 | 0.2863 | 7.8802 |
| HS4.69R | 0.4233 | 0.5767 | 0.1664 | 0.0889 | 0.3583 | 3.3091 |
| 1766 | 0.4196 | 0.5804 | 0.1679 | 0.0911 | 0.3401 | 3.7750 |
| 2250 | 0.7327 | 0.2673 | 0.0697 | 0.0114 | 0.2724 | 12.1803 |
| MLS18 | 0.3803 | 0.6197 | 0.1849 | 0.1200 | 0.4375 | 2.3331 |
| NBC13 | 0.4032 | 0.5968 | 0.1746 | 0.1017 | 0.3807 | 2.9129 |
| NBC51 | 0.3796 | 0.6204 | 0.1852 | 0.1205 | 0.4408 | 2.3105 |
| 2265 | 0.3858 | 0.6142 | 0.1823 | 0.1151 | 0.4162 | 2.5044 |
| Combined 15 loci | $4.16 \times 10^{-6}$ | 0.999996 | 0.9284 | 0.7548 | $3.12 \times 10^{-7}$ | 130 million |

The results indicated that most of the markers follow Hardy Weinberg Equilibrium. Since the populations samples were from Mother and Father of Paternity cases and samples were collected from a rural county, relatedness among donors could be a possibility, further analysis using random DNA samples obtained from unrelated individuals are needed to confirm whether to eliminate few of the markers to make the multiplex more suitable for forensic and paternity applications. However, the preliminary data indicate that a 15-20 marker multiplexed RE will provide high Paternity index and high power of discrimination and can be successfully used for paternity application as a standalone marker system.

Population and statistical analysis were performed with either GDA software (Lewis, P. O., et al., *Genetic Data Analysis: Computer program for the analysis of allelic data*, Version 1.0 (2001)), Arlequin 3.11 (Excoffier, L., et al., *Arlequin (version 3.0): an integrated software package for population genetics data analysis*, Evolutionary Bioinformatics Online, 1: 47 (2005)), or in-house developed software. Departures from Hardy-Weinberg equilibrium (HWE) and linkage equilibrium were tested using Fisher's exact test. Bonferroni's correction for multiple comparisons was performed according to Weir and Cockerham [33]. Results are shown in Table 8.

TABLE 8

Allele Frequencies of Markers

| Markers | Alias | Marker Type | Caucasian Probability $P_E$ | $P_F$ | Allele Frequency $a^2$ | 2ab | $b^2$ | African American Probability $P_E$ | $P_F$ | Allele Frequency $a^2$ | 2ab | $b^2$ |
|---|---|---|---|---|---|---|---|---|---|---|---|---|
| LC3-2601 | L2601 | Ancestry | 0.016 | 0.984 | 3E-04 | 0.032 | 0.968 | 0.523 | 0.477 | 0.273 | 0.499 | 0.228 |
| Yac52265 | 2265 | Forensic | 0.247 | 0.753 | 0.061 | 0.372 | 0.567 | 0.72 | 0.28 | 0.518 | 0.403 | 0.079 |
| CH14-50-6236 | 6236 | Forensic | 0.726 | 0.274 | 0.527 | 0.398 | 0.075 | 0.488 | 0.512 | 0.238 | 0.5 | 0.262 |
| CH4-12-7012 | 7012 | Ancestry | 0.022 | 0.979 | 5E-04 | 0.042 | 0.957 | 0.198 | 0.802 | 0.039 | 0.317 | 0.644 |
| Y5ac2305 | 2305 | Forensic | 0.441 | 0.559 | 0.194 | 0.493 | 0.312 | 0.755 | 0.245 | 0.57 | 0.37 | 0.06 |
| Ya5NBC51 | 51 | Forensic | 0.467 | 0.533 | 0.218 | 0.498 | 0.284 | 0.421 | 0.58 | 0.177 | 0.487 | 0.336 |
| Yb7AD155 | 155 | Forensic | 0.544 | 0.456 | 0.296 | 0.496 | 0.208 | 0.587 | 0.413 | 0.345 | 0.485 | 0.17 |
| CH6-28-9163 | 9163 | Ancestry | 0.467 | 0.533 | 0.218 | 0.498 | 0.284 | 0.758 | 0.242 | 0.575 | 0.367 | 0.058 |
| Yb8NBC106 | 106 | Forensic | 0.5 | 0.5 | 0.25 | 0.5 | 0.25 | 0.449 | 0.551 | 0.202 | 0.495 | 0.303 |
| Yb8AC1141 | 1141 | Forensic | 0.39 | 0.61 | 0.152 | 0.476 | 0.372 | | | | | |
| Ya5-MLS48 | MLS48 | Forensic | 0.206 | 0.794 | 0.042 | 0.327 | 0.63 | 0.628 | 0.372 | 0.394 | 0.467 | 0.138 |
| TARBP1R | TARBP1 | Forensic | 0.436 | 0.565 | 0.19 | 0.492 | 0.319 | 0.683 | 0.317 | 0.467 | 0.433 | 0.1 |
| HS4.69R | HS4.69R | Forensic | 0.59 | 0.41 | 0.348 | 0.484 | 0.168 | | | | | |
| CHR22-19250 | 9250 | Forensic | 0.34 | 0.66 | 0.116 | 0.449 | 0.436 | | | | | |
| Yb8AC1796 | 1796 | Forensic | 0.63 | 0.37 | 0.397 | 0.466 | 0.137 | | | | | |
| CHR20-79712 | 9712 | Forensic | 0.51 | 0.49 | 0.26 | 0.5 | 0.24 | | | | | |
| CH1-6217R | 6217R | Forensic | 0.69 | 0.31 | 0.476 | 0.428 | 0.096 | 0.539 | 0.461 | 0.291 | 0.497 | 0.213 |
| Ya5ACA1766 | 1766 | Forensic | 0.32 | 0.68 | 0.102 | 0.435 | 0.462 | | | | | |
| pAlu-19-2139 | 2139 | Forensic | 0.54 | 0.46 | 0.292 | 0.497 | 0.212 | | | | | |
| Ya5-MLS18R | MLS18R | Forensic | 0.39 | 0.61 | 0.152 | 0.476 | 0.372 | | | | | |
| MLS9 | MLS9 | Forensic | 0.54 | 0.46 | 0.292 | 0.497 | 0.212 | | | | | |
| YA5-MLS26 | MLS26 | Forensic | 0.55 | 0.45 | 0.303 | 0.495 | 0.203 | | | | | |
| AC4027 | 4027 | Forensic | 0.58 | 0.42 | 0.336 | 0.487 | 0.176 | | | | | |

Example 9

Study of the Effectiveness of the Multiplex Reaction Using Degraded DNA Samples Five single source DNA samples were sonicated up to eight hours. One ng input DNA was amplified with the 15 RE+Amelegenin multiplex small amplicon DNA typing system offered by InnoGenomics and referred to Inno-Typer™ and compared to the STR DNA typing kits PowerPlex® 16HS, Identifiler® Plus and Minifiler™ using 3130 Genetic Analyzer (Applied Biosystems).

InnoTyper™ produced results at more loci for the degraded samples than the STR kits and therefore, outperformed all three STR kits tested, including MiniFiler™. This data shows the InnoTyper™ kit is highly successful over any STR kit currently used in the market.

In more detail, the degradation study was conducted as follows. An ultrasonic cleaning device provided the method for mechanically shearing the DNA samples into fragments. The device was filled with distilled water and set at 50° C. Volumes of 30 μL of extracted DNA, from three different samples, were sonicated for up to eight hours. Additionally, two treatment levels of DNase I provided the enzymatic method of cleaving genomic material and severely decreased the DNA sample quality. Samples underwent 10 units of DNase I treatment for 30 minutes at 37° C. and 100 units of DNase I treatment for 20 minutes at 37° C. The DNase reaction was stopped by the addition of 0.5 M EDTA, and samples were purified using the Microcon YM-30 (Millipore Corp) and eluted with TE buffer. In order to test the effectiveness of the primers on degraded DNA, Inno-Typer markers were used, as their amplicon lengths are no greater than 125 bp. The degraded samples were amplified under previously described conditions. A corresponding non-degraded DNA sample served as the positive control.

Example 10

Sensitivity Study of the Multiplex Reaction

All markers selected for the above multiplex reaction produced full profiles using 0.5 to 0.2 ng/μL DNA concentrations. At 0.1 ng/μL, all markers except Y5ac2305 displayed full profiles. At 0.05 ng/μL, all but six markers displayed full profiles. Markers CH4-12-7012, LC3-2601 and CH1-6217 displayed partial profiles, while Yb7AD155, Y5ac2305 and Yb8NBC106 displayed no profiles. Results showed the 200 pg range to be the optimum DNA concentration for further analysis. A summary of average peak height for all markers is graphically represented in FIG. 12. A full 16 marker DNA profile was obtained from as low as 40 pg of total DNA when amplified using the InnoTyper™ 15 marker RE and Amelogenin multiplex.

The above multiplex system, the small amplicon DNA typing system offered by InnoGenomics and referred to as InnoTyper™, was further evaluated for intra and inter RE peak height balance and sensitivity of detection. Peak heights of the 300 database samples were analyzed. Homozygous peak heights were divided by 2. Some loci had higher peak heights than others, but on the average, all peaks fell between 1000-2000 RFU when 1 ng of total DNA target sample was used. FIG. 6 demonstrates the peak height analysis of 150 database samples.

Heterozygosity percentages of the database samples were also examined. With the exception of MLS48, all markers produced heterozygous peaks above 70% heterozygosity (see FIG. 7). MLS48 was above 50%.

Heterozygous DNA profiles for each marker were diluted in 10 mM TE Buffer (pH 8.0) to obtain the following concentrations: 0.5, 0.2, 0.1 and 0.05 ng/μL. The dilutions were amplified with the following markers under previously described conditions. Table 9 shows that peak intensities were similar in magnitude for most pairs of corresponding empty and filled alleles.

TABLE 9

Primer Optimization using 2 μL primer mix. For each genetic marker, amplicon length, peak height ratio and peak intensity were determined.

| Markers | Alias | Reverse E primer size* (bp) | Reverse F primer size* (bp) | Peak Ratio (Empty:Filled) | Peak Intensity at 0.25 ng DNA (RFU) |
|---|---|---|---|---|---|
| CH1-6217 | 6217 | 161 | 156 | 1:2 | 1200:1200 |
| LC3-2601 | L2601 | 177 | 123 | 1:2 | 2000:800 |
| Yac52265 | 2265 | 104 | 100 | 1:1 | 1600:1200 |
| CH14-50-6236 | 6236 | 176 | 123 | 1:2.5 | 1400:1400 |
| CH4-12-7012 | 7012 | 152 | 123 | 1:1 | 1300:1700 |
| Y5ac2305 | 2305 | 58.5 | 60 | 1:1 | 1000:1300 |
| Ya5NBC51 | 51 | 119 | 118.5 | 1:1 | 1600:1600 |
| Yb7AD155 | 155 | 99 | 98.5 | 1:1 | 1500:1200 |
| CH6-28-9163 | 9163 | 112 | 112.5 | 1:1 | 1300:1300 |
| CH2-5-6240 | 6240 | 149 | 127 | 1:3 | 1800:1500 |
| Yb8NBC106 | 106 | 122 | 117.5 | 1:1 | 1200:1100 |
| Ya5ACA1736 | 1736 | 109 | 105 | 1:1 | 1250:1200 |
| HS4.69R | HS4.69R | 110 | 103 | 1:1 | 800:800 |
| Yb8AC1141 | 1141 | 60 | 56 | 1:1.5 | 1200:800 |
| Ya5-MLS48 | MLS48 | 82 | 76 | 1:1 | 1400:1300 |
| CH1-2250 | 2250 | 102 | 100 | 1:1 | 1000:1100 |
| Yb8NBC13 | 13 | 96 | 89 | 1:1 | 1000:1000 |
| TARBP1 | TARBP1 | 55 | 49 | 1.5:1 | 900:1600 |

Asterisk (*) indicates the amplicon bp sizes based on the 310 Genetic Analyzer.

Example 11

Species Specificity Study

To determine any cross-reactivity with nonhuman species, DNA from various nonhuman species was extracted and amplified with the InnoTyper™ 16 multiplex. The following species were tested with the total input DNA shown in Table 10.

TABLE 10

Types and amounts of DNA used to evaluate species specificity of the 15 RE multiplex.

| Species | Input DNA |
|---|---|
| Human | 1 ng |
| Chimpanzee | 1 ng |
| Orangutan | 1 ng |
| Vero Monkey | 1 ng |
| Deer | 10 ng |
| Cat | 10 ng |
| Dog | 10 ng |
| Mouse | 10 ng |
| Chicken | 10 ng |
| Mosquito | 10 ng |
| Staph | 10 ng |

Some cross reactivity was observed with the nonhuman primate species tested (chimpanzee, orangutan, and vero monkey). Nonspecific peaks were observed with some mammalian species (cat and deer). See FIG. 13 for results.

While this invention has been particularly shown and described with reference to embodiments thereof, it will be understood by those skilled in the art that various changes in form and details may be made therein without departing from the spirit and scope of the invention as defined by the appended claims.

What is claimed is:

1. A method for genetic detection, comprising:
providing a sample;
selecting fifteen to nineteen Retrotransposable element (RE) markers plus Amelogenin, each selected RE marker being an INNUL marker that is associated with both a filled allele representing a filled genomic site and an empty allele representing an empty genomic site, each INNUL marker comprising a nucleic acid sequence, the nucleic acid sequence being found at a location within the human genome, the RE markers being selected from the group consisting of CHR20-79712, Ya5-MLS48, Yb8NBC13, Ya5ACA1736, Yb8NBC106, Y5ac2305, HS4.69, AC4027, CH1-6217, Yb8AC1796, Yac52265, MLS9, TARBP1, SVA306, SVA323, Ya5NBC51, Yb8AC1141, Yb7AD155 and Ya5-MLS18;
providing a forward primer and a reverse primer, each corresponding to Amelogenin;
providing a primer set corresponding to each selected INNUL marker, each primer set consisting of a forward primer and two reverse primers, one of the forward primer of each primer set and the reverse primers of each primer set comprising an observable label, the two reverse primers consisting of a primer corresponding to a filled site of the INNUL marker and a primer corresponding to an empty site of the INNUL marker, the primer sets being selected from the following, each primer set being indicated by a genomic marker name, a forward primer sequence, a reverse empty primer sequence and a reverse filled primer sequence: CHR20-79712, ATTTGCACAGTGCTCCACAC (SEQ ID NO: 1), GTTGCACGTAAGACAGAATTTGA (SEQ ID NO: 2), GCGGCCAAGACAGAATTTGA (SEQ ID NO: 3); Ya5-MLS48, TTGGCTTGTAAACTAATTGCTG (SEQ ID NO: 4), GCAAAGCAACTTGCACCTTTTCTA (SEQ ID NO: 5), GCGGCCGCACCTTTTCTATTG (SEQ ID NO: 6); Yb8NBC13, TCTGGCAAATGCTACCCAAGT (SEQ ID NO: 7), GCTGAAGCATCTTCCTCTTCACA (SEQ ID NO: 8), GCGGCCCCTCTTCACATCTTA (SEQ ID NO: 9); Ya5ACA1736, CCTGCTCTGCACACTTCTTG (SEQ ID NO: 10), GACCTTGACCTAGAGAAGGCAAT (SEQ ID NO: 11), GCCGAGAAGGCAATTTTCTA (SEQ ID NO: 12); Yb8NBC106, CATCAAACTCCAGAGTTCCTAAG (SEQ ID NO: 13), GATTGATGAGGACTCAGGTTGA (SEQ ID NO: 14), GGATTACAGGCGTGAGGATT (SEQ ID NO: 15); Y5ac2305, TGGTGACACTCCAATTTCTTCT (SEQ ID NO: 16), GGCATCCTTTGATTACAACTCTTA (SEQ ID NO: 17), GCCCCAATTACAACTCTTAAGGAAA (SEQ ID NO: 18); HS4.69, TGCCAGGTGATAGTATTAGGAGGTG (SEQ ID NO: 19), GGCATCGTATCTATTCATGTGATTTTA (SEQ ID NO: 20), CCGGCCTATTCATGTGATTT (SEQ ID NO: 21); AC4027, AAGGTCTAAGCGCAGTGGAA (SEQ ID NO: 22), GTGTTTTGTACAGAGTTCTTAATTGC (SEQ ID NO: 23), GGCCCAGAGTTCTTAATTGC (SEQ ID NO: 24); CH1-6217, TGGCCCACCTATGTCTAAAA (SEQ ID NO: 25), GTTGATTCAAAGCAACCAATCC (SEQ ID NO: 26), GTCAAGGCAAACCAATCCAA (SEQ ID NO: 27); Yb8AC1796, TGCCAGACAGCAAACAAATA (SEQ ID NO: 28), GCAAGGTCACAGGTAGGCTTTTA (SEQ ID NO: 29), GGCCACAGGTAGGCTTTTA (SEQ ID NO: 30); Yac52265, AGAAGAGTGAATGCACATTTATGA (SEQ ID NO: 31), GGAGTCATGAATTCAGTTTCTTA (SEQ ID NO: 32), GCCCGGCCCAGTTTCTTA (SEQ ID NO: 33); MLS9, AGCAGATTTCAGGTCATTATTGTTT (SEQ ID NO: 34), GTTTCTCTCAGAAGCTATCTCAATTTTAA (SEQ ID NO: 35), GCGGCCTGCTATCTCAATTT (SEQ ID NO: 36); TARBP1, AAGGAGGCAAAGGAAGAATACA (SEQ ID NO: 37), GTTGATCCAGTCATTCATCATTTTAT (SEQ ID NO: 38), GCGGCCCATTCATCAGTTT (SEQ ID NO: 39); SVA306, TGGAGGCCTCTGCTATTTTC (SEQ ID NO: 40), GAAGGGTTCATTAAAGAATTTTCATAG (SEQ ID NO: 41), GAGAGGGAGAGGGACAAGAA (SEQ ID NO: 42); Amelogenin, CCCTTTGAAGTGGTACCAGAGCA (SEQ ID NO: 43), GCATGCCTAATATTTTCAGGGAATA (SEQ ID NO: 44), (only two primers used for Amelogenin); SVA323, TGTGCTTCATTTGAGAAAGCTG (SEQ ID NO: 46), GCTGGCCGGAAGTCTTAATGC (SEQ ID NO: 47), GTTGAAGGATAGAAGTCTTAATGCAG (SEQ ID NO: 48); Ya5NBC51, TCGCCATCTCTTCTTCCTTCA (SEQ ID NO: 49), GTCCAGGGTTAATGCTTTGT (SEQ ID NO: 50), GACAGGCGTGAGAATGCTTTG (SEQ ID NO: 51); Yb8AC1141, ACAAATACTACAGACAAAAGCTACTGA (SEQ ID NO: 52), GAACCCCACCAACCTGACT (SEQ ID NO: 53), GGCCCAACCTGACTTACT (SEQ ID NO: 54); Yb7AD155, TGTACACATTAAGCACATGGAAGTCA (SEQ ID NO: 55), GCATGAAATGTTCTTTTTCATCT (SEQ ID NO: 56), GCCCGGCCGTTCTTTTTC (SEQ ID NO: 57); Ya5-MLS18, AACTTCAAGGTATTTGCATCATG (SEQ ID NO: 58), TGCTAGCTAACTCTCTAAGGTCTT (SEQ ID NO: 59), CCGGCCTCTAAGGTCTTTTT (SEQ ID NO: 60);

combining the primer sets with the sample to form a reaction mixture;

amplifying all of the selected markers simultaneously using the primer sets in the reaction mixture to form a mixture of amplification products, each primer set generating an amplicon corresponding to a filled allele and an amplicon corresponding to an empty allele, no amplicon generated from a selected marker having a size outside of a range of from 46 to 124 base pairs;

separating the amplification products from the remainder of the reaction mixture; and detecting and quantitating each labeled amplification product.

2. The method of claim 1, each forward primer having a structure additionally comprising an observable label.

3. The method of claim 2, the observable labels being fluorescent organic dyes.

4. The method of claim 3, the observable labels being selected from 6-carboxyfluorescein (sold as 6-FAM), 6-carboxy-4',5'-dichloro-2',7'-dimethoxyfluorescein (sold as JOE), 6-carboxytetramethylrhodamine (sold as TAMRA) and a label comprising at least one of 5-carboxy-X-rhodamine and 6-carboxy-X-rhodamine (sold as ROX).

5. The method of claim 1, each reverse primer having a structure additionally comprising an observable label.

6. The method of claim 5, the observable labels being fluorescent organic dyes.

7. The method of claim 6, the observable labels being selected from 6-carboxyfluorescein (sold as 6-FAM), 6-carboxy-4',5'-dichloro-2',7'-dimethoxyfluorescein (sold as JOE), 6-carboxytetramethylrhodamine (sold as TAMRA) and a label comprising at least one of 5-carboxy-X-rhodamine and 6-carboxy-X-rhodamine (sold as ROX).

8. The method of claim 1, the amplifying step including the use of a real-time polymerase chain reaction (PCR) system.

9. The method of claim 1, each amplification product being labeled with a distinct observable label.

10. The method of claim 1, the selected RE markers being selected from the group consisting of Alus and LINEs.

11. The method of claim 1, the plurality of RE markers being selected for human identity testing.

12. The method of claim 1, the plurality of RE markers being selected for bio-ancestry studies.

13. The method of claim 1, the labeled amplification products being detected and quantitated for samples comprising as little as 100 pg of DNA.

14. The method of claim 1, each selected RE marker comprising a Target Site Duplication (TSD) sequence, each reverse primer comprising a nucleic acid sequence that includes all or part of the TSD sequence.

15. The method of claim 1, the separating step comprising the use of electrophoresis.

16. A multiplexed DNA analysis system, the system comprising:

a sample of DNA;

a set of fifteen to nineteen INNUL markers plus Amelogenin, each INNUL marker comprising a filled allele and an empty allele;

a set of three primers corresponding to each INNUL marker, each set of primers including a forward primer and two reverse primers, the forward primer including a detectable label, one reverse primer corresponding to the filled allele and the other reverse primer corresponding to the empty allele, the primer sets being selected from the following, each primer set being indicated by a genomic marker name, a forward primer sequence, a reverse empty primer sequence and a reverse filled primer sequence: CHR20-79712, [6-FAM]ATTTGCACAGTGCTCCACAC (SEQ ID NO: 61), GTTGCACGTAAGACAGAATTTGA (SEQ ID NO: 2), GCGGCCAAGACAGAATTTGA (SEQ ID NO: 3); Ya5-MLS48, [6-FAM]TTGGCTTG-TAAACTAATTGCTG (SEQ ID NO: 62), GCAAAGCAACTTGCACCTTTTCTA (SEQ ID NO: 5), GCGGCCGCACCTTTTCTATTG (SEQ ID NO: 6); Yb8NBC13, [6-FAM]TCTGGCAAATGCTAC-CCAAGT (SEQ ID NO: 63), GCTGAAGCATCTTC-CTCTTCACA (SEQ ID NO: 8), GCGGCCCCTCT-TCACATCTTA (SEQ ID NO: 9); Ya5ACA1736, [6-FAM]CCTGCTCTGCACACTTCTTG (SEQ ID NO: 64), GACCTTGACCTAGAGAAGGCAAT (SEQ ID NO: 11), GCCGAGAAGGCAATTTTCTA (SEQ ID NO: 12); Yb8NBC106, [6-FAM]CATCAAACTC-CAGAGTTCCTAAG (SEQ ID NO: 65), GATTGAT-GAGGACTCAGGTTGA (SEQ ID NO: 14), GGAT-TACAGGCGTGAGGATT (SEQ ID NO: 15); Y5ac2305, [JOE]TGGTGACACTCCAATTTCTTCT (SEQ ID NO: 66), GGCATCCTTTGATTA-CAACTCTTA (SEQ ID NO: 17), GCCCCAATTA-CAACTCTTAAGGAAA (SEQ ID NO: 18); HS4.69, [ROX]TGCCAGGTGATAGTATTAGGAGGTG (SEQ ID NO: 67), GGCATCGTATCTATTCATGT-GATTTTA (SEQ ID NO: 20), CCGGCCTATTCAT-GTGATTT (SEQ ID NO: 21); AC4027, [JOE] AAGGTCTAAGCGCAGTGGAA (SEQ ID NO: 68), GTGTTTTGTACAGAGTTCTTAATTGC (SEQ ID NO: 23), GGCCCAGAGTTCTTAATTGC (SEQ ID NO: 24); CH1-6217, [JOE]TGGCCCACCTAT-GTCTAAAA (SEQ ID NO: 69), GTTGAT-TCAAAGCAACCAATCC (SEQ ID NO: 26), GTCAAGGCAAACCAATCCAA (SEQ ID NO: 27); Yb8AC1796, [JOE]TGCCAGACAGCAAACAAATA (SEQ ID NO: 70), GCAAGGTCACAGGTAG-GCTTTTTA (SEQ ID NO: 29), GGCCACAGGTAG-GCTTTTTA (SEQ ID NO: 30); Yac52265, [JOE] AGAAGAGTGAATGCACATTATGA (SEQ ID NO: 71), GGAGTCATGAATTCAGTTTCTTA (SEQ ID NO: 32), GCCCGGCCCAGTTTCTTA (SEQ ID NO: 33); MLS9, [JOE]AGCAGATTTCAGGTCATTATT-GTTT (SEQ ID NO: 72), GTTTCTCTCAGAAGC-TATCTCAATTTTAA (SEQ ID NO: 35), GCGGCCT-GCTATCTCAATTT (SEQ ID NO: 36); TARBP1, [TMR]AAGGAGGCAAAGGAAGAATACA (SEQ ID NO: 73), GTTGATCCAGTCATTCATCATTTTAT (SEQ ID NO: 38), GCGGCCCATTCATCAGTTT (SEQ ID NO: 39); SVA306, [TMR]TGGAGGCCTCT-GCTATTTTC (SEQ ID NO: 74), GAAGGGTTCAT-TAAAGAATTTTCATAG (SEQ ID NO: 41), GAGAGGGAGAGGGACAAGAA (SEQ ID NO: 42); Amelogenin, [TMR]CCCTTTGAAGTGGTACCA-GAGCA (SEQ ID NO: 75), GCATGCCTAAT-ATTTTCAGGGAATA (SEQ ID NO: 44), (only two primers used for Amelogenin); SVA323, [TMR]TGT-GCTTCATTTGAGAAAGCTG (SEQ ID NO: 76), GCTGGCCGGAAGTCTTAATGC (SEQ ID NO: 47), GTTGAAGGATAGAAGTCTTAATGCAG (SEQ ID NO: 48); Ya5NBC51, [ROX]TCGCCATCTCTTCT-TCCTTCA (SEQ ID NO: 77), GTCCAGGGTTAAT-GCTTTGT (SEQ ID NO: 50), GACAGGCGT-GAGAATGCTTTG (SEQ ID NO: 51); Yb8AC1141, [ROX]ACAAATACTACAGACAAAAGCTACTGA (SEQ ID NO: 78), GAACCCCACCAACCTGACT (SEQ ID NO: 53), GGCCCAACCTGACTTACT (SEQ ID NO: 54); Yb7AD155, [ROX]TGTACACAT-TAAGCACATGGAAGTCA (SEQ ID NO: 79), GCAT-GAAATGTTCTTTTTCATCT (SEQ ID NO: 56), GCCCGGCCGTTCTTTTTC (SEQ ID NO: 57); Ya5-MLS18, [ROX]AACTTCAAGGTATTTGCATCATG (SEQ ID NO: 80), TGCTAGCTAACTCTCTAAGGTCTT (SEQ ID NO: 59), CCGGCCTCTAAGGTCTTTTT (SEQ ID NO: 60);

a polymerase chain reaction (PCR) amplification system that simultaneously produces PCR amplification products corresponding to each INNUL marker of the set, each primer set generating a PCR amplicon corresponding to a filled allele and a PCR amplicon corresponding to an empty allele, no PCR amplicon generated from the INNUL markers of the set having a size outside of a range of from about 46 to about 124 pairs;

means for separating PCR amplification products from reactants and from each other;

means for detecting and quantitating PCR amplification products using the detectable label; and means for deriving a useful forensic-related or bioancestry-related conclusion from the quantitative PCR results.

17. The system of claim 16, the means for separating PCR amplification products being electrophoresis.

18. The system of claim 16, the set of INNUL markers consisting of 15 INNUL markers plus Amelogenin.

19. The system of claim 16, the detectable labels being selected from a group of four fluorescent organic dyes.

20. The system of claim 16, the amplification products being characterized by Next Generation Sequence analysis (NGS) methods.

21. The system of claim 16, the amplification products being characterized by rapid DNA analysis platforms.

22. The method of claim 1, the separating and detecting/quantitating steps comprising Next Generation Sequence analysis (NGS) methods.

23. The method of claim 1, the separating and detecting/quantitating steps comprising use of rapid DNA analysis platforms.

24. The method of claim 1, the amplifying step being carried out using a polymerase chain reaction (PCR) technique.

25. A method for genetic detection, comprising:

providing a sample;

selecting nineteen Retrotransposable element (RE) markers plus Amelogenin, each selected RE marker being an INNUL marker that is associated with both a filled allele representing a filled genomic site and an empty allele representing an empty genomic site, each INNUL marker comprising a nucleic acid sequence, the nucleic acid sequence being found at a location within the human genome, the RE markers being CHR20-79712, Ya5-MLS48, Yb8NBC13, Ya5ACA1736, Yb8NBC106, Y5ac2305, HS4.69, AC4027, CH1-6217, Yb8AC1796, Yac52265, MLS9, TARBP1, SVA306, SVA323, Ya5NBC51, Yb8AC1141, Yb7AD155 and Ya5-MLS18;

providing a forward primer and a reverse primer, each corresponding to Amelogenin;

providing a primer set corresponding to each selected INNUL marker, each primer set consisting of a forward primer and two reverse primers, one of the forward primer of each primer set and the reverse primers of each primer set comprising an observable label, the two reverse primers consisting of a primer corresponding to a filled site of the INNUL marker and a primer corresponding to an empty site of the INNUL marker, the primer sets being as follows: each primer set being indicated by a genomic marker name, a forward primer sequence, a reverse empty primer sequence and a reverse filled primer sequence: CHR20-79712, ATTTGCACAGTGCTCCACAC (SEQ ID NO: 1), GTTGCACGTAAGACAGAATTTGA (SEQ ID NO: 2), GCGGCCAAGACAGAATTTGA (SEQ ID NO: 3); Ya5-MLS48, TTGGCTTGTAAACTAATTGCTG (SEQ ID NO: 4), GCAAAGCAACTTGCACCTTTTCTA (SEQ ID NO: 5), GCGGCCGCACCTTTTCTATTG (SEQ ID NO: 6); Yb8NBC13, TCTGGCAAATGCTACCCAAGT (SEQ ID NO: 7), GCTGAAGCATCTTCCTCTTCACA (SEQ ID NO: 8), GCGGCCCCTCTTCACATCTTA (SEQ ID NO: 9); Ya5ACA1736, CCTGCTCTGCACACTTCTTG (SEQ ID NO: 10), GACCTTGACCTAGAGAAGGCAAT (SEQ ID NO: 11), GCCGAGAAGGCAATTTTCTA (SEQ ID NO: 12); Yb8NBC106, CATCAAACTCCAGAGTTCCTAAG (SEQ ID NO: 13), GATTGATGAGGACTCAGGTTGA (SEQ ID NO: 14), GGATTACAGGCGTGAGGATT (SEQ ID NO: 15); Y5ac2305, TGGTGACACTCCAATTTCTTCT (SEQ ID NO: 16), GGCATCCTTTGATTACAACTCTTA (SEQ ID NO: 17), GCCCCAATTACAACTCTTAAGGAAA (SEQ ID NO: 18); HS4.69, TGCCAGGTGATAGTATTAGGAGGTG (SEQ ID NO: 19), GGCATCGTATCTATTCATGTGATTTTTA (SEQ ID NO: 20), CCGGCCTATTCATGTGATTT (SEQ ID NO: 21); AC4027, AAGGTCTAAGCGCAGTGGAA (SEQ ID NO: 22), GTGTTTTGTACAGAGTTCTTAATTGC (SEQ ID NO: 23), GGCCCAGAGTTCTTAATTGC (SEQ ID NO: 24); CH1-6217, TGGCCCACCTATGTCTAAAA (SEQ ID NO: 25), GTTGATTCAAAGCAACCAATCC (SEQ ID NO: 26), GTCAAGGCAAACCAATCCAA (SEQ ID NO: 27); Yb8AC1796, TGCCAGACAGCAAACAAATA (SEQ ID NO: 28), GCAAGGTCACAGGTAGGCTTTTA (SEQ ID NO: 29), GGCCACAGGTAGGCTTTTA (SEQ ID NO: 30); Yac52265, AGAAGAGTGAATGCACATTTATGA (SEQ ID NO: 31), GGAGTCATGAATTCAGTTTCTTA (SEQ ID NO: 32), GCCCGGCCCAGTTTCTTA (SEQ ID NO: 33); MLS9, AGCAGATTTCAGGTCATTATTGTTT (SEQ ID NO: 34), GTTTCTCTCAGAAGCTATCTCAATTTAA (SEQ ID NO: 35), GCGGCCTGCTATCTCAATTT (SEQ ID NO: 36); TARBP1, AAGGAGGCAAAGGAAGAATACA (SEQ ID NO: 37), GTTGATCCAGTCATTCATCATTTTAT (SEQ ID NO: 38), GCGGCCCATTCATCAGTTT (SEQ ID NO: 39); SVA306, TGGAGGCCTCTGCTATTTC (SEQ ID NO: 40), GAAGGGTTCATTAAAGAATTTTCATAG (SEQ ID NO: 41), GAGAGGGAGAGGGACAAGAA (SEQ ID NO: 42); Amelogenin, CCCTTTGAAGTGGTACCAGAGCA (SEQ ID NO: 43), GCATGCCTAATATTTTCAGGGAATA (SEQ ID NO: 44), (only two primers used for Amelogenin); SVA323, TGTGCTTCATTTGAGAAAGCTG (SEQ ID NO: 46), GCTGGCCGGAAGTCTTAATGC (SEQ ID NO: 47), GTTGAAGGATAGAAGTCTTAATGCAG (SEQ ID NO: 48); Ya5NBC51, TCGCCATCTCTTCTTCCTTCA (SEQ ID NO: 49), GTCCAGGGTTAATGCTTTGT (SEQ ID NO: 50), GACAGGCGTGAGAATGCTTTG (SEQ ID NO: 51); Yb8AC1141, ACAAATACTACAGACAAAAGCTACTGA (SEQ ID NO: 52), GAACCCCACCAACCTGACT (SEQ ID NO: 53), GGCCCAACCTGACTTACT (SEQ ID NO: 54); Yb7AD155, TGTACACATTAAGCACATGGAAGTCA (SEQ ID NO: 55), GCATGAAATGTTCTTTTTCATCT (SEQ ID NO: 56), GCCCGGCCGTTCTTTTTC (SEQ ID NO: 57); Ya5-MLS18, AACTTCAAGGTATTTGCATCATG (SEQ ID NO: 58), TGCTAGCTAACTCTCTAAGGTCTT (SEQ ID NO: 59), CCGGCCTCTAAGGTCTTTTT (SEQ ID NO: 60);

combining the primer sets with the sample to form a reaction mixture;

amplifying all of the selected markers simultaneously using the primer sets in the reaction mixture to form a mixture of amplification products, each primer set generating an amplicon corresponding to a filled allele and an amplicon corresponding to an empty allele, no amplicon generated from a selected marker having a size outside of a range of from 46 to 124 base pairs;

separating the amplification products from the remainder of the reaction mixture; and detecting and quantitating each labeled amplification product.

26. The method of claim 25, the amplifying step including the use of a real-time polymerase chain reaction (PCR) system.

27. The method of claim 25, the labeled amplification products being detected and quantitated for samples comprising as little as 100 pg of DNA.

28. The method of claim 25, where the sample comprises 500 pg of a DNA standard.

29. The method of claim 25, the separating step comprising the use of electrophoresis.

30. The method of claim 25, the separating and detecting/quantitating steps comprising Next Generation Sequence analysis (NGS) methods.

31. The method of claim 25, the separating and detecting/quantitating steps comprising use of rapid DNA analysis platforms.

* * * * *

```
                           SEQUENCE LISTING

<160> NUMBER OF SEQ ID NOS: 82

<210> SEQ ID NO 1
<211> LENGTH: 20
<212> TYPE: DNA
<213> ORGANISM: Artificial
<220> FEATURE:
<223> OTHER INFORMATION: A forward primer for CHR20-79712, a human
      genetic marker that is useful for genetic detection for forensic
      or bio-ancestry studies.

<400> SEQUENCE: 1
atttgcacag tgctccacac                                            20

<210> SEQ ID NO 2
<211> LENGTH: 23
<212> TYPE: DNA
<213> ORGANISM: Artificial
<220> FEATURE:
<223> OTHER INFORMATION: Reverse primier for empty sequence for CHR20-
      79712, a human genetic marker that is useful for genetic detection
      for forensic or bio-ancestry studies.

<400> SEQUENCE: 2
gttgcacgta agacagaatt tga                                        23

<210> SEQ ID NO 3
<211> LENGTH: 20
<212> TYPE: DNA
<213> ORGANISM: Artificial
<220> FEATURE:
<223> OTHER INFORMATION: Reverse primer for filled sequence for CHR20-
      79712, a human genetic marker that is useful for genetic detection
      for forensic or bio-ancestry studies.

<400> SEQUENCE: 3
gcggccaaga cagaatttga                                            20

<210> SEQ ID NO 4
<211> LENGTH: 22
<212> TYPE: DNA
<213> ORGANISM: Artificial
<220> FEATURE:
<223> OTHER INFORMATION: Forward primer for Ya5-MLS48, a human genetic
      marker that is useful for genetic detection for forensic or bio-
      ancestry studies.

<400> SEQUENCE: 4
ttggcttgta aactaattgc tg                                         22

<210> SEQ ID NO 5
<211> LENGTH: 24
<212> TYPE: DNA
<213> ORGANISM: Artificial
<220> FEATURE:
<223> OTHER INFORMATION: Reverse primer for empty sequence for Ya5-
      MLS48, a human genetic marker that is useful for genetic detection
      for forensic or bio-ancestry studies.

<400> SEQUENCE: 5
gcaaagcaac ttgcaccttt tcta                                       24

<210> SEQ ID NO 6
```

-continued

```
<211> LENGTH: 21
<212> TYPE: DNA
<213> ORGANISM: Artificial
<220> FEATURE:
<223> OTHER INFORMATION: Reverse primer for filled sequence for Ya5-
      MLS48, a human genetic marker that is useful for genetic detection
      for forensic or bio-ancestry studies.

<400> SEQUENCE: 6
gcggccgcac cttttctatt g                                              21

<210> SEQ ID NO 7
<211> LENGTH: 21
<212> TYPE: DNA
<213> ORGANISM: Artificial
<220> FEATURE:
<223> OTHER INFORMATION: Forward primer for Yb8NBC13, a human genetic
      marker that is useful for genetic detection for forensic or bio-
      ancestry studies.

<400> SEQUENCE: 7
tctggcaaat gctacccaag t                                              21

<210> SEQ ID NO 8
<211> LENGTH: 23
<212> TYPE: DNA
<213> ORGANISM: Artificial
<220> FEATURE:
<223> OTHER INFORMATION: Reverse primer for empty sequence for Yb8NBC13,
      a human genetic marker that is useful for genetic detection for
      forensic or bio-ancestry studies.

<400> SEQUENCE: 8
gctgaagcat cttcctcttc aca                                            23

<210> SEQ ID NO 9
<211> LENGTH: 21
<212> TYPE: DNA
<213> ORGANISM: Artificial
<220> FEATURE:
<223> OTHER INFORMATION: Reverse primer for filled sequence for
      Yb8NBC13, a human genetic marker that is useful for genetic
      detection for forensic or bio-ancestry studies.

<400> SEQUENCE: 9
gcggcccctc ttcacatctt a                                              21

<210> SEQ ID NO 10
<211> LENGTH: 20
<212> TYPE: DNA
<213> ORGANISM: Artificial
<220> FEATURE:
<223> OTHER INFORMATION: Forward primer for Ya5ACA1736, a human genetic
      marker that is useful for genetic detection for forensic or bio-
      ancestry studies.

<400> SEQUENCE: 10
cctgctctgc acacttcttg                                                20

<210> SEQ ID NO 11
<211> LENGTH: 23
<212> TYPE: DNA
<213> ORGANISM: Artificial
<220> FEATURE:
<223> OTHER INFORMATION: Reverse primer for empty sequence for
      Ya5ACA1736, a human genetic marker that is useful for genetic
      detection for forensic or bio-ancestry studies.

<400> SEQUENCE: 11
```
gaccttgacc tagagaaggc aat                                                    23

<210> SEQ ID NO 12
<211> LENGTH: 20
<212> TYPE: DNA
<213> ORGANISM: Artificial
<220> FEATURE:
<223> OTHER INFORMATION: Reverse primer for filled sequence for
    Ya5ACA1736, a human genetic marker that is useful for genetic
    detection for forensic or bio-ancestry studies.

<400> SEQUENCE: 12
gccgagaagg caattttcta                                                        20

<210> SEQ ID NO 13
<211> LENGTH: 23
<212> TYPE: DNA
<213> ORGANISM: Artificial
<220> FEATURE:
<223> OTHER INFORMATION: Forward primer for Yb8NBC106, a human genetic
    marker that is useful for genetic detection for forensic or bio-
    ancestry studies.

<400> SEQUENCE: 13
catcaaactc cagagttcct aag                                                    23

<210> SEQ ID NO 14
<211> LENGTH: 22
<212> TYPE: DNA
<213> ORGANISM: Artificial
<220> FEATURE:
<223> OTHER INFORMATION: Reverse primer for empty sequence for
    Yb8NBC106, a human genetic marker that is useful for genetic
    detection for forensic or bio-ancestry studies.

<400> SEQUENCE: 14
gattgatgag gactcaggtt ga                                                     22

<210> SEQ ID NO 15
<211> LENGTH: 20
<212> TYPE: DNA
<213> ORGANISM: Artificial
<220> FEATURE:
<223> OTHER INFORMATION: Reverse primer for filled sequence for
    Yb8NBC106, a human genetic marker that is useful for genetic
    detection for forensic or bio-ancestry studies.

<400> SEQUENCE: 15
ggattacagg cgtgaggatt                                                        20

<210> SEQ ID NO 16
<211> LENGTH: 22
<212> TYPE: DNA
<213> ORGANISM: Artificial
<220> FEATURE:
<223> OTHER INFORMATION: Forward primer for Y5ac2305, a human genetic
    marker that is useful for genetic detection for forensic or bio-
    ancestry studies.

<400> SEQUENCE: 16
tggtgacact ccaatttctt ct                                                     22

<210> SEQ ID NO 17
<211> LENGTH: 24
<212> TYPE: DNA
<213> ORGANISM: Artificial
<220> FEATURE:

<223> OTHER INFORMATION: Reverse primer for empty sequence for Y5ac2305,
      a human genetic marker that is useful for genetic detection for
      forensic or bio-ancestry studies.

<400> SEQUENCE: 17 ggcatcctttt gattacaact ctta                                          24

<210> SEQ ID NO 18
<211> LENGTH: 25
<212> TYPE: DNA
<213> ORGANISM: Artificial
<220> FEATURE:
<223> OTHER INFORMATION: Reverse primer for filled sequence for
      Y5ac2305, a human genetic marker that is useful for genetic
      detection for forensic or bio-ancestry studies.

<400> SEQUENCE: 18
gccccaatta caactcttaa ggaaa                                          25

<210> SEQ ID NO 19
<211> LENGTH: 25
<212> TYPE: DNA
<213> ORGANISM: Artificial
<220> FEATURE:
<223> OTHER INFORMATION: Forward primer for HS4.69, a human genetic
      marker that is useful for genetic detection for forensic or bio-
      ancestry studies.

<400> SEQUENCE: 19
tgccaggtga tagtattagg aggtg                                          25

<210> SEQ ID NO 20
<211> LENGTH: 28
<212> TYPE: DNA
<213> ORGANISM: Artificial
<220> FEATURE:
<223> OTHER INFORMATION: Reverse primer for empty sequence for HS4.69,
      a human genetic marker that is useful for genetic detection for
      forensic or bio-ancestry studies.

<400> SEQUENCE: 20
ggcatcgtat ctattcatgt gattttta                                       28

<210> SEQ ID NO 21
<211> LENGTH: 20
<212> TYPE: DNA
<213> ORGANISM: Artificial
<220> FEATURE:
<223> OTHER INFORMATION: Reverse primer for filled sequence for HS4.69,
      a human genetic marker that is useful for genetic detection for
      forensic or bio-ancestry studies.

<400> SEQUENCE: 21
ccggcctatt catgtgattt                                                20

<210> SEQ ID NO 22
<211> LENGTH: 20
<212> TYPE: DNA
<213> ORGANISM: Artificial
<220> FEATURE:
<223> OTHER INFORMATION: Forward primer for AC4027, a human genetic
      marker that is useful for genetic detection for forensic or bio-
      ancestry studies.

<400> SEQUENCE: 22
aaggtctaag cgcagtggaa                                                20

<210> SEQ ID NO 23
<211> LENGTH: 26
<212> TYPE: DNA
<213> ORGANISM: Artificial
<220> FEATURE:
<223> OTHER INFORMATION: Reverse primer for empty sequence for AC4027, a human genetic marker that is useful for genetic detection for forensic or bio-ancestry studies.

<400> SEQUENCE: 23
gtgttttgta cagagttctt aattgc                                          26

<210> SEQ ID NO 24
<211> LENGTH: 20
<212> TYPE: DNA
<213> ORGANISM: Artificial
<220> FEATURE:
<223> OTHER INFORMATION: Reverse primer for filled sequence for AC4027, a human genetic marker that is useful for genetic detection for forensic or bio-ancestry studies.

<400> SEQUENCE: 24
ggcccagagt tcttaattgc                                                 20

<210> SEQ ID NO 25
<211> LENGTH: 20
<212> TYPE: DNA
<213> ORGANISM: Artificial
<220> FEATURE:
<223> OTHER INFORMATION: Forward primer for CH1-6217, a human genetic marker that is useful for genetic detection for forensic or bio-ancestry studies.

<400> SEQUENCE: 25
tggcccacct atgtctaaaa                                                 20

<210> SEQ ID NO 26
<211> LENGTH: 22
<212> TYPE: DNA
<213> ORGANISM: Artificial
<220> FEATURE:
<223> OTHER INFORMATION: Reverse primer for empty sequence for CH1-6217, a human genetic marker that is useful for genetic detection for forensic or bio-ancestry studies.

<400> SEQUENCE: 26
gttgattcaa agcaaccaat cc                                              22

<210> SEQ ID NO 27
<211> LENGTH: 20
<212> TYPE: DNA
<213> ORGANISM: Artificial
<220> FEATURE:
<223> OTHER INFORMATION: Reverse primer for filled sequence for CH1-6217, a human genetic marker that is useful for genetic detection for forensic or bio-ancestry studies.

<400> SEQUENCE: 27
gtcaaggcaa accaatccaa                                                 20

<210> SEQ ID NO 28
<211> LENGTH: 20
<212> TYPE: DNA
<213> ORGANISM: Artificial
<220> FEATURE:
<223> OTHER INFORMATION: Forward primer for Yb8AC1796, a human genetic marker that is useful for genetic detection for forensic or bio-ancestry studies.

```
<400> SEQUENCE: 28
tgccagacag caaacaaata                                            20

<210> SEQ ID NO 29
<211> LENGTH: 24
<212> TYPE: DNA
<213> ORGANISM: Artificial
<220> FEATURE:
<223> OTHER INFORMATION: Reverse primer for empty sequence for
      Yb8AC1796, a human genetic marker that is useful for genetic
      detection for forensic or bio-ancestry studies.

<400> SEQUENCE: 29
gcaaggtcac aggtaggctt ttta                                       24

<210> SEQ ID NO 30
<211> LENGTH: 20
<212> TYPE: DNA
<213> ORGANISM: Artificial
<220> FEATURE:
<223> OTHER INFORMATION: Reverse primer for filled sequence for
      Yb8AC1796, a human genetic marker that is useful for genetic
      detection for forensic or bio-ancestry studies.

<400> SEQUENCE: 30
ggccacaggt aggcttttta                                            20

<210> SEQ ID NO 31
<211> LENGTH: 24
<212> TYPE: DNA
<213> ORGANISM: Artificial
<220> FEATURE:
<223> OTHER INFORMATION: Forward primer for Yac52265, a human genetic
      marker that is useful for genetic detection for forensic or bio-
      ancestry studies.

<400> SEQUENCE: 31
agaagagtga atgcacattt atga                                       24

<210> SEQ ID NO 32
<211> LENGTH: 23
<212> TYPE: DNA
<213> ORGANISM: Artificial
<220> FEATURE:
<223> OTHER INFORMATION: Reverse primer for empty sequence for Yac52265,
      a human genetic marker that is useful for genetic detection for
      forensic or bio-ancestry studies.

<400> SEQUENCE: 32
ggagtcatga attcagtttc tta                                        23

<210> SEQ ID NO 33
<211> LENGTH: 18
<212> TYPE: DNA
<213> ORGANISM: Artificial
<220> FEATURE:
<223> OTHER INFORMATION: Reverse primer for filled sequence for
      Yac52265, a human genetic marker that is useful for genetic
      detection for forensic or bio-ancestry studies.

<400> SEQUENCE: 33
gcccggccca gtttctta                                              18

<210> SEQ ID NO 34
<211> LENGTH: 25
<212> TYPE: DNA
<213> ORGANISM: Artificial
```

```
<220> FEATURE:
<223> OTHER INFORMATION: Forward primer for MLS9, a human genetic marker
      that is useful for genetic detection for forensic or bio-ancestry
      studies.

<400> SEQUENCE: 34
agcagatttc aggtcattat tgttt                                         25

<210> SEQ ID NO 35
<211> LENGTH: 29
<212> TYPE: DNA
<213> ORGANISM: Artificial
<220> FEATURE:
<223> OTHER INFORMATION: Reverse primer for empty sequence for MLS9, a
      human genetic marker that is useful for genetic detection for
      forensic or bio-ancestry studies.

<400> SEQUENCE: 35
gtttctctca gaagctatct caattttaa                                     29

<210> SEQ ID NO 36
<211> LENGTH: 20
<212> TYPE: DNA
<213> ORGANISM: Artificial
<220> FEATURE:
<223> OTHER INFORMATION: Reverse primer for filled sequence for MLS9, a
      human genetic marker that is useful for genetic detection for
      forensic or bio-ancestry studies.

<400> SEQUENCE: 36
gcggcctgct atctcaattt                                               20

<210> SEQ ID NO 37
<211> LENGTH: 22
<212> TYPE: DNA
<213> ORGANISM: Artificial
<220> FEATURE:
<223> OTHER INFORMATION: Forward primer for TARBP1, a human genetic
      marker that is useful for genetic detection for forensic or bio-
      ancestry studies.

<400> SEQUENCE: 37
aaggaggcaa aggaagaata ca                                            22

<210> SEQ ID NO 38
<211> LENGTH: 26
<212> TYPE: DNA
<213> ORGANISM: Artificial
<220> FEATURE:
<223> OTHER INFORMATION: Reverse primer for empty sequence for TARBP1, a
      human genetic marker that is useful for genetic detection for
      forensic or bio-ancestry studies.

<400> SEQUENCE: 38
gttgatccag tcattcatca ttttat                                        26

<210> SEQ ID NO 39
<211> LENGTH: 19
<212> TYPE: DNA
<213> ORGANISM: Artificial
<220> FEATURE:
<223> OTHER INFORMATION: Reverse primer for filled sequence for TARBP1,
      a human genetic marker that is useful for genetic detection for
      forensic or bio-ancestry studies.

<400> SEQUENCE: 39
gcggcccatt catcagttt                                                19
```

```
<210> SEQ ID NO 40
<211> LENGTH: 20
<212> TYPE: DNA
<213> ORGANISM: Artificial
<220> FEATURE:
<223> OTHER INFORMATION: Forward primer for SVA306, a human genetic
      marker that is useful for genetic detection for forensic or bio-
      ancestry studies.

<400> SEQUENCE: 40
tggaggcctc tgctattttc                                              20

<210> SEQ ID NO 41
<211> LENGTH: 27
<212> TYPE: DNA
<213> ORGANISM: Artificial
<220> FEATURE:
<223> OTHER INFORMATION: Reverse primer for empty sequence for SVA306,
      a human genetic marker that is useful for genetic detection for
      forensic or bio-ancestry studies.

<400> SEQUENCE: 41
gaagggttca ttaaagaatt ttcatag                                      27

<210> SEQ ID NO 42
<211> LENGTH: 20
<212> TYPE: DNA
<213> ORGANISM: Artificial
<220> FEATURE:
<223> OTHER INFORMATION: Reverse primer for filled sequence for SVA306,
      a human genetic marker that is useful for genetic detection for
      forensic or bio-ancestry studies.

<400> SEQUENCE: 42
gagagggaga gggacaagaa                                              20

<210> SEQ ID NO 43
<211> LENGTH: 23
<212> TYPE: DNA
<213> ORGANISM: Artificial
<220> FEATURE:
<223> OTHER INFORMATION: Forward primer for Amelogenin

<400> SEQUENCE: 43
ccctttgaag tggtaccaga gca                                          23

<210> SEQ ID NO 44
<211> LENGTH: 25
<212> TYPE: DNA
<213> ORGANISM: Artificial
<220> FEATURE:
<223> OTHER INFORMATION: Reverse primer for empty sequence for
      Amelogenin

<400> SEQUENCE: 44
gcatgcctaa tattttcagg gaata                                        25

<210> SEQ ID NO 45
<211> LENGTH: 0
<212> TYPE: DNA
<213> ORGANISM: Artificial
<220> FEATURE:
<223> OTHER INFORMATION: Reverse primer for filled sequence for
      Amelogenin

<400> SEQUENCE: 45

000
```

<210> SEQ ID NO 46
<211> LENGTH: 22
<212> TYPE: DNA
<213> ORGANISM: Artificial
<220> FEATURE:
<223> OTHER INFORMATION: Forward primer for SVA323, a human genetic
    marker that is useful for genetic detection for forensic or bio-
    ancestry studies.

<400> SEQUENCE: 46
tgtgcttcat ttgagaaagc tg                                          22

<210> SEQ ID NO 47
<211> LENGTH: 21
<212> TYPE: DNA
<213> ORGANISM: Artificial
<220> FEATURE:
<223> OTHER INFORMATION: Reverse primer for empty sequence for SVA323, a
    human genetic marker that is useful for genetic detection for
    forensic or bio-ancestry studies.

<400> SEQUENCE: 47
gctggccgga agtcttaatg c                                           21

<210> SEQ ID NO 48
<211> LENGTH: 26
<212> TYPE: DNA
<213> ORGANISM: Artificial
<220> FEATURE:
<223> OTHER INFORMATION: Reverse primer for filled sequence for SVA323,
    a human genetic marker that is useful for genetic detection for
    forensic or bio-ancestry studies.

<400> SEQUENCE: 48
gttgaaggat agaagtctta atgcag                                      26

<210> SEQ ID NO 49
<211> LENGTH: 21
<212> TYPE: DNA
<213> ORGANISM: Artificial
<220> FEATURE:
<223> OTHER INFORMATION: Forward primer for Ya5NBC51, a human genetic
    marker that is useful for genetic detection for forensic or bio-
    ancestry studies.

<400> SEQUENCE: 49
tcgccatctc ttcttccttc a                                           21

<210> SEQ ID NO 50
<211> LENGTH: 20
<212> TYPE: DNA
<213> ORGANISM: Artificial
<220> FEATURE:
<223> OTHER INFORMATION: Reverse primer for empty sequence for Ya5NBC51,
    a human genetic marker that is useful for genetic detection for
    forensic or bio-ancestry studies.

<400> SEQUENCE: 50
gtccagggtt aatgctttgt                                             20

<210> SEQ ID NO 51
<211> LENGTH: 21
<212> TYPE: DNA
<213> ORGANISM: Artificial
<220> FEATURE:
<223> OTHER INFORMATION: Reverse primer for filled sequence for
    Ya5NBC51, a human genetic marker that is useful for genetic detection for forensic or bio-ancestry studies.

<400> SEQUENCE: 51
gacaggcgtg agaatgcttt g					21

<210> SEQ ID NO 52
<211> LENGTH: 27
<212> TYPE: DNA
<213> ORGANISM: Artificial
<220> FEATURE:
<223> OTHER INFORMATION: Forward primer for Yb8AC1141, a human genetic
      marker that is useful for genetic detection for forensic or bio-
      ancestry studies.

<400> SEQUENCE: 52
acaaatacta cagacaaaag ctactga					27

<210> SEQ ID NO 53
<211> LENGTH: 19
<212> TYPE: DNA
<213> ORGANISM: Artificial
<220> FEATURE:
<223> OTHER INFORMATION: Reverse primer for empty sequence for
      Yb8AC1141, a human genetic marker that is useful for genetic
      detection for forensic or bio-ancestry studies.

<400> SEQUENCE: 53
gaaccccacc aacctgact					19

<210> SEQ ID NO 54
<211> LENGTH: 18
<212> TYPE: DNA
<213> ORGANISM: Artificial
<220> FEATURE:
<223> OTHER INFORMATION: Reverse primer for filled sequence for
      Yb8AC1141, a human genetic marker that is useful for genetic
      detection for forensic or bio-ancestry studies.

<400> SEQUENCE: 54
ggcccaacct gacttact					18

<210> SEQ ID NO 55
<211> LENGTH: 26
<212> TYPE: DNA
<213> ORGANISM: Artificial
<220> FEATURE:
<223> OTHER INFORMATION: Forward primer for Yb7AD155, a human genetic
      marker that is useful for genetic detection for forensic or bio-
      ancestry studies.

<400> SEQUENCE: 55
tgtacacatt aagcacatgg aagtca					26

<210> SEQ ID NO 56
<211> LENGTH: 23
<212> TYPE: DNA
<213> ORGANISM: Artificial
<220> FEATURE:
<223> OTHER INFORMATION: Reverse primer for empty sequence for Yb7AD155,
      a human genetic marker that is useful for genetic detection for
      forensic or bio-ancestry studies.

<400> SEQUENCE: 56
gcatgaaatg ttcttttca tct					23

<210> SEQ ID NO 57
<211> LENGTH: 18

```
<212> TYPE: DNA
<213> ORGANISM: Artificial
<220> FEATURE:
<223> OTHER INFORMATION: Reverse primer for filled sequence for
      Yb7AD155, a human genetic marker that is useful for genetic
      detection for forensic or bio-ancestry studies.

<400> SEQUENCE: 57
gcccggccgt tcttttc                                                      18

<210> SEQ ID NO 58
<211> LENGTH: 23
<212> TYPE: DNA
<213> ORGANISM: Artificial
<220> FEATURE:
<223> OTHER INFORMATION: Forward primer for Ya5-MLS18, a human genetic
      marker that is useful for genetic detection for forensic or bio-
      ancestry studies.

<400> SEQUENCE: 58
aacttcaagg tatttgcatc atg                                               23

<210> SEQ ID NO 59
<211> LENGTH: 24
<212> TYPE: DNA
<213> ORGANISM: Artificial
<220> FEATURE:
<223> OTHER INFORMATION: Reverse primer for empty sequence for
      Ya5-MLS18, a human genetic marker that is useful for genetic
      detection for forensic or bio-ancestry studies.

<400> SEQUENCE: 59
tgctagctaa ctctctaagg tctt                                              24

<210> SEQ ID NO 60
<211> LENGTH: 20
<212> TYPE: DNA
<213> ORGANISM: Artificial
<220> FEATURE:
<223> OTHER INFORMATION: Reverse primer for filled sequence for
      Ya5-MLS18, a human genetic marker that is useful for genetic
      detection for forensic or bio-ancestry studies.

<400> SEQUENCE: 60
ccggcctcta aggtctttt                                                    20

<210> SEQ ID NO 61
<211> LENGTH: 20
<212> TYPE: DNA
<213> ORGANISM: Artificial
<220> FEATURE:
<223> OTHER INFORMATION: Labeled forward primer for CHR20-79712. The
      "n" is to be replaced with adenine modified with 6-FAM dye.
<220> FEATURE:
<221> NAME/KEY: misc_feature
<222> LOCATION: (1)..(1)
<223> OTHER INFORMATION: n is a, c, g, or t

<400> SEQUENCE: 61
ntttgcacag tgctccacac                                                   20

<210> SEQ ID NO 62
<211> LENGTH: 22
<212> TYPE: DNA
<213> ORGANISM: Artificial
<220> FEATURE:
<223> OTHER INFORMATION: Labeled forward primer for Ya5-MLS48. The "n"
      is to be replaced with a thymine modified with 6-FAM dye.
<220> FEATURE:
```

<221> NAME/KEY: misc_feature
<222> LOCATION: (1)..(1)
<223> OTHER INFORMATION: n is a, c, g, or t

<400> SEQUENCE: 62
ntggcttgta aactaattgc tg    22

<210> SEQ ID NO 63
<211> LENGTH: 21
<212> TYPE: DNA
<213> ORGANISM: Artificial
<220> FEATURE:
<223> OTHER INFORMATION: Labeled forward primer for Yb8NBC13. The "n"
      is to be replaced by thymine modified with 6-FAM dye.
<220> FEATURE:
<221> NAME/KEY: misc_feature
<222> LOCATION: (1)..(1)
<223> OTHER INFORMATION: n is a, c, g, or t

<400> SEQUENCE: 63
nctggcaaat gctacccaag t    21

<210> SEQ ID NO 64
<211> LENGTH: 20
<212> TYPE: DNA
<213> ORGANISM: Artificial
<220> FEATURE:
<223> OTHER INFORMATION: Labeled forward primer for Ya5ACA1736. The "n"
      is to be replaced with a cytosine labeled with 6-FAM dye.
<220> FEATURE:
<221> NAME/KEY: misc_feature
<222> LOCATION: (1)..(1)
<223> OTHER INFORMATION: n is a, c, g, or t

<400> SEQUENCE: 64
nctgctctgc acacttcttg    20

<210> SEQ ID NO 65
<211> LENGTH: 23
<212> TYPE: DNA
<213> ORGANISM: Artificial
<220> FEATURE:
<223> OTHER INFORMATION: Labeled forward primer for Yb8NBC106. The "n"
      is to be replaced with a cytosine labeled with 6-FAM dye.
<220> FEATURE:
<221> NAME/KEY: misc_feature
<222> LOCATION: (1)..(1)
<223> OTHER INFORMATION: n is a, c, g, or t

<400> SEQUENCE: 65
natcaaactc cagagttcct aag    23

<210> SEQ ID NO 66
<211> LENGTH: 22
<212> TYPE: DNA
<213> ORGANISM: Artificial
<220> FEATURE:
<223> OTHER INFORMATION: Labeled forward primer for Y5ac2305. The "n"
      is to be replaced with a thymine labeled with JOE dye.
<220> FEATURE:
<221> NAME/KEY: misc_feature
<222> LOCATION: (1)..(1)
<223> OTHER INFORMATION: n is a, c, g, or t

<400> SEQUENCE: 66
nggtgacact ccaatttctt ct    22

<210> SEQ ID NO 67
<211> LENGTH: 25

```
<212> TYPE: DNA
<213> ORGANISM: Artificial
<220> FEATURE:
<223> OTHER INFORMATION: Labeled forward primer for HS4.69.  The "n" is
      to be replaced with thymine labeled with ROX dye.
<220> FEATURE:
<221> NAME/KEY: misc_feature
<222> LOCATION: (1)..(1)
<223> OTHER INFORMATION: n is a, c, g, or t

<400> SEQUENCE: 67
ngccaggtga tagtattagg aggtg                                            25

<210> SEQ ID NO 68
<211> LENGTH: 20
<212> TYPE: DNA
<213> ORGANISM: Artificial
<220> FEATURE:
<223> OTHER INFORMATION: Labeled forward primer for AC4027.  The "n" is
      to be replaced with an adenine labeled with JOE dye.
<220> FEATURE:
<221> NAME/KEY: misc_feature
<222> LOCATION: (1)..(1)
<223> OTHER INFORMATION: n is a, c, g, or t

<400> SEQUENCE: 68
naggtctaag cgcagtggaa                                                  20

<210> SEQ ID NO 69
<211> LENGTH: 20
<212> TYPE: DNA
<213> ORGANISM: Artificial
<220> FEATURE:
<223> OTHER INFORMATION: Labeled forward primer for CH1-6217.  The "n"
      is to be replaced with a thymine labeled with JOE dye.
<220> FEATURE:
<221> NAME/KEY: misc_feature
<222> LOCATION: (1)..(1)
<223> OTHER INFORMATION: n is a, c, g, or t

<400> SEQUENCE: 69
nggcccacct atgtctaaaa                                                  20

<210> SEQ ID NO 70
<211> LENGTH: 20
<212> TYPE: DNA
<213> ORGANISM: Artificial
<220> FEATURE:
<223> OTHER INFORMATION: Labeled forward primer for Yb8AC1796.  The "n"
      is to be replaced with a thymine labeled with JOE dye.
<220> FEATURE:
<221> NAME/KEY: misc_feature
<222> LOCATION: (1)..(1)
<223> OTHER INFORMATION: n is a, c, g, or t

<400> SEQUENCE: 70
ngccagacag caaacaaata                                                  20

<210> SEQ ID NO 71
<211> LENGTH: 24
<212> TYPE: DNA
<213> ORGANISM: Artificial
<220> FEATURE:
<223> OTHER INFORMATION: Labeled forward primer for Yac52265.  The "n"
      is to be replaced with an adenine labeled with JOE dye.
<220> FEATURE:
<221> NAME/KEY: misc_feature
<222> LOCATION: (1)..(1)
<223> OTHER INFORMATION: n is a, c, g, or t

<400> SEQUENCE: 71
```

-continued ngaagagtga atgcacattt atga                                          24

<210> SEQ ID NO 72
<211> LENGTH: 25
<212> TYPE: DNA
<213> ORGANISM: Artificial
<220> FEATURE:
<223> OTHER INFORMATION: Labeled forward primer for MLS9. The "n" is to
      be replaced with an adenine labeled with JOE dye.
<220> FEATURE:
<221> NAME/KEY: misc_feature
<222> LOCATION: (1)..(1)
<223> OTHER INFORMATION: n is a, c, g, or t

<400> SEQUENCE: 72
ngcagatttc aggtcattat tgttt                                         25

<210> SEQ ID NO 73
<211> LENGTH: 22
<212> TYPE: DNA
<213> ORGANISM: Artificial
<220> FEATURE:
<223> OTHER INFORMATION: Labeled forward primer for TARBP1. The "n" is
      to be replaced with an adenine labeled with TAMRA dye.
<220> FEATURE:
<221> NAME/KEY: misc_feature
<222> LOCATION: (1)..(1)
<223> OTHER INFORMATION: n is a, c, g, or t

<400> SEQUENCE: 73
naggaggcaa aggaagaata ca                                            22

<210> SEQ ID NO 74
<211> LENGTH: 20
<212> TYPE: DNA
<213> ORGANISM: Artificial
<220> FEATURE:
<223> OTHER INFORMATION: Labeled forward primer for SVA306. The "n" is
      to be replaced with a thymine labeled with TAMRA dye.
<220> FEATURE:
<221> NAME/KEY: misc_feature
<222> LOCATION: (1)..(1)
<223> OTHER INFORMATION: n is a, c, g, or t

<400> SEQUENCE: 74
nggaggcctc tgctattttc                                               20

<210> SEQ ID NO 75
<211> LENGTH: 23
<212> TYPE: DNA
<213> ORGANISM: Artificial
<220> FEATURE:
<223> OTHER INFORMATION: Labeled forward primer for Amelogenin. The "n"
      is to be replaced with a cytosine labeled with TAMRA dye.
<220> FEATURE:
<221> NAME/KEY: misc_feature
<222> LOCATION: (1)..(1)
<223> OTHER INFORMATION: n is a, c, g, or t

<400> SEQUENCE: 75
ncctttgaag tggtaccaga gca                                           23

<210> SEQ ID NO 76
<211> LENGTH: 22
<212> TYPE: DNA
<213> ORGANISM: Artificial
<220> FEATURE:
<223> OTHER INFORMATION: Labeled forward primer for SVA323. The "n" is
      to be replaced by a thymine labeled with TAMRA dye.

-continued

```
<220> FEATURE:
<221> NAME/KEY: misc_feature
<222> LOCATION: (1)..(1)
<223> OTHER INFORMATION: n is a, c, g, or t

<400> SEQUENCE: 76
ngtgcttcat ttgagaaagc tg                                              22

<210> SEQ ID NO 77
<211> LENGTH: 21
<212> TYPE: DNA
<213> ORGANISM: Artificial
<220> FEATURE:
<223> OTHER INFORMATION: Labeled forward primer for Ya5NBC51. The "n"
      is to be replaced by a thymine labeled with ROX dye.
<220> FEATURE:
<221> NAME/KEY: misc_feature
<222> LOCATION: (1)..(1)
<223> OTHER INFORMATION: n is a, c, g, or t

<400> SEQUENCE: 77
ncgccatctc ttcttccttc a                                               21

<210> SEQ ID NO 78
<211> LENGTH: 27
<212> TYPE: DNA
<213> ORGANISM: Artificial
<220> FEATURE:
<223> OTHER INFORMATION: Labeled forward primer for Yb8AC1141. The "n"
      is to be replaced by an adenine labeled with ROX dye.
<220> FEATURE:
<221> NAME/KEY: misc_feature
<222> LOCATION: (1)..(1)
<223> OTHER INFORMATION: n is a, c, g, or t

<400> SEQUENCE: 78
ncaaatacta cagacaaaag ctactga                                         27

<210> SEQ ID NO 79
<211> LENGTH: 26
<212> TYPE: DNA
<213> ORGANISM: Artificial
<220> FEATURE:
<223> OTHER INFORMATION: Labeled forward primer for Yb7AD155. The "n"
      is to be replaced with a thymine labeled with ROX dye.
<220> FEATURE:
<221> NAME/KEY: misc_feature
<222> LOCATION: (1)..(1)
<223> OTHER INFORMATION: n is a, c, g, or t

<400> SEQUENCE: 79
ngtacacatt aagcacatgg aagtca                                          26

<210> SEQ ID NO 80
<211> LENGTH: 23
<212> TYPE: DNA
<213> ORGANISM: Artificial
<220> FEATURE:
<223> OTHER INFORMATION: Labeled forward primer for Ya5-MLS18. The "n"
      is to be replaced by an adenine labeled with ROX dye.
<220> FEATURE:
<221> NAME/KEY: misc_feature
<222> LOCATION: (1)..(1)
<223> OTHER INFORMATION: n is a, c, g, or t

<400> SEQUENCE: 80
nacttcaagg tatttgcatc atg                                             23

<210> SEQ ID NO 81
```

```
<211> LENGTH: 749
<212> TYPE: DNA
<213> ORGANISM: Homo sapiens
<220> FEATURE:
<223> OTHER INFORMATION: Filled Site Reaction of marker Ya5ac2305

<400> SEQUENCE: 81
caaactatcg gtataatctt ctaatttgtc tcattataaa gtattctatt tctataggac      60
aggttaataa tccagaaaaa tgaaactaag atgatcaaaa cctgtagtta atactttaaa     120
atacaatcca acaccattta atcttctgag ttggtgacac tccaatttct tctctctaac     180
gtttccttaa gagttgtaat tggggccggg cgcggtggct cacgcctgta atcccagcac     240
tttgggaggc cgaggcgggc ggatcatgag gtcaggagat cgagaccatc ccggctaaaa     300
cggtgaaacc ccgtctctac taaaaataca aaaaattagc cgggcgtagt ggcgggcgcc     360
tgtagtccca gctacttggg aggctgaggc aggagaatgg cgtgaacccg ggaggcggag     420
cttacagtga gccgagatcc cgccactgca ctccagcctg ggcgacagag cgagactccg     480
tctcaaaaaa aaaaaaaaaa aaaaaaaaaa aagagttgta atcaaaggat gcctgggtaa     540
gagctgggtt tggttttggt acttaggtct tttggtaatt ccattttagc accactgaat     600
tatcattagt gctttaaaga gctgcctttt gtggatagaa tgaattatta tacatattca     660 tcattttgt cttcctactg atacatttaa ggagtggaga tacaatattt tcatccaata     720
ggtcacaatg catataattg ctgacattt                                      749

<210> SEQ ID NO 82
<211> LENGTH: 419
<212> TYPE: DNA
<213> ORGANISM: Homo sapiens
<220> FEATURE:
<223> OTHER INFORMATION: Empty Site Reaction of marker Ya5ac2305

<400> SEQUENCE: 82
caaactatcg gtataatctt ctaatttgtc tcattataaa gtattctatt tctataggac      60
aggttaataa tccagaaaaa tgaaactaag atgatcaaaa cctgtagtta atactttaaa     120
atacaatcca acaccattta atcttctgag ttggtgacac tccaatttct tctctctaac     180
gtttccttaa gagttgtaat caaaggatgc ctgggtaaga gctgggtttg gttttggtac     240
ttaggtcttt tggtaattcc attttagcac cactgaatta tcattagtgc tttaaagagc     300
tgccttttgt ggatagaatg aattattata catattcatc attttgtct tcctactgat     360 acatttaagg agtggagata caatattttc atccaatagg tcacaatgca tataattgc     419
```